United States Patent
Zhao et al.

(10) Patent No.: US 9,896,517 B2
(45) Date of Patent: Feb. 20, 2018

(54) LOW MOLECULAR WEIGHT GLYCOSAMINOGLYCAN DERIVATIVE, PHARMACEUTICAL COMPOSITION THEREOF, PREPARATION METHOD THEREFOR AND USE THEREOF

(71) Applicant: Jiuzhitang Co., Ltd., Changsha, Hunan (CN)

(72) Inventors: Jinhua Zhao, Yunnan (CN); Jikai Liu, Yunnan (CN); Mingyi Wu, Yunnan (CN); Na Gao, Yunnan (CN); Feng Lu, Yunnan (CN); Zi Li, Yunnan (CN)

(73) Assignee: Jiuzhitang Co., Ltd., Changsha (CN)

( * ) Notice: Subject to any disclaimer, the term of this patent is extended or adjusted under 35 U.S.C. 154(b) by 0 days.

(21) Appl. No.: 14/778,966

(22) PCT Filed: Dec. 20, 2013

(86) PCT No.: PCT/CN2013/090131
§ 371 (c)(1),
(2) Date: Sep. 21, 2015

(87) PCT Pub. No.: WO2014/153995
PCT Pub. Date: Oct. 2, 2014

(65) Prior Publication Data
US 2016/0039949 A1    Feb. 11, 2016

(30) Foreign Application Priority Data

Mar. 26, 2013  (CN) .......................... 2013 1 0099800

(51) Int. Cl.
*C08B 37/00* (2006.01)
*A61K 9/00* (2006.01)
*A61K 31/726* (2006.01)

(52) U.S. Cl.
CPC ........ *C08B 37/0063* (2013.01); *A61K 9/0019* (2013.01); *A61K 31/726* (2013.01); *C08B 37/00* (2013.01)

(58) Field of Classification Search
CPC .... A61K 31/726; A61K 9/0019; C08B 37/00; C08B 37/0063
USPC ..................................... 514/52, 62; 536/55.2
See application file for complete search history.

(56) References Cited

FOREIGN PATENT DOCUMENTS

| CN | 1852926 | A | 10/2006 |
| CN | 102329397 | A | 1/2012 |
| CN | 102558389 | A * | 7/2012 |
| CN | 103145868 | A | 6/2013 |
| WO | 2011138512 | A1 | 11/2002 |
| WO | 2010078511 | A2 | 7/2010 |

OTHER PUBLICATIONS

Liu et al.; CN 102558389 A; Jul. 11, 2012 (Machine English Translation).*
Gao et al. (Mar. Drugs 2012, 10, 1647-1661).*

* cited by examiner

*Primary Examiner* — Shaojia Anna Jiang
*Assistant Examiner* — Michael C Henry
(74) *Attorney, Agent, or Firm* — Maschoff Brennan

(57) ABSTRACT

Provided are a low-molecular-weight fucosylated glycosaminoglycan derivative (derivative of Low molecular weight Fucosylated Glycosaminoglycan, dLFG) having anticoagulant activity, a preparation method thereof, a pharmaceutical composition comprising dLFG or a pharmaceutically acceptable salt thereof, and the use of dLFG and pharmaceutical composition thereof in preparing medicine for treating thrombotic diseases.

8 Claims, 8 Drawing Sheets

FGAG
│ converted to +H type by ion exchange method (Dowex/r50w ×8 50-100(H))
│ neutralized by quaternary ammonium base titration, lyophilized
▼
FGAG quaternary ammonium salt
│ with 1-Chloro-3-methyl-2-butene in DMF
│ reacted at 40°C under stirring, isolated and lyophilized to obtain product
▼
FGAG methacrylate ester
│ after +H conversion, titrated with tetrabutylammonium hydroxide solution
│ concentrated, lyophilized
▼
FGAG methacrylate ester tetrabutylammonium salt
│ dissolved in DMF (10mg/ml) and added with freshly prepared sodium ethylate-
│ ethanol solution (40mM)
│ reacted at room temperature, added with equal volume of water and stirred,
│ isolated and lyophilized to obtain product
▼
dLFG

Fig.12

LOW MOLECULAR WEIGHT GLYCOSAMINOGLYCAN DERIVATIVE, PHARMACEUTICAL COMPOSITION THEREOF, PREPARATION METHOD THEREFOR AND USE THEREOF

FIELD OF THE INVENTION

The present invention belongs to the field of medical technology, and particularly relates to a low-molecular-weight fucosylated glycosaminoglycan derivative (derivative of Low molecular weight Fucosylated Glycosaminoglycan, dLFG) having anticoagulant activity, a preparation method thereof, a pharmaceutical composition comprising the dLFG or a pharmaceutically acceptable salt thereof, and the use of the dLFG and pharmaceutical compositions thereof in preparing medicine for treating thrombotic diseases.

BACKGROUND OF THE INVENTION

Thromboembolic diseases including ischemic stroke, coronary heart disease, and venous thromboembolism are the major lethal causes of human beings. Antithrombotic drug therapy is the basic means in the clinical prevention and treatment of thrombotic diseases; however, antithrombotic drugs including fibrinolytic, anticoagulant and antiplatelet agents all have the main and common defects: bleeding tendency and severe hemorrhage risk.

Classic anticoagulants heparins (f.IIa/Xa inhibitors) and coumarins (vitamin K antagonists) were clinically used since the 30s and 40s of the last century and were the cornerstone of therapeutic drugs for deep vein thrombosis, cardiac stroke and postoperative anticoagulant over the past 70-plus years, however, the risk of bleeding and pharmacodynamic/pharmacokinetic defects seriously limited their clinical application. Heparin and coumarin drugs widely inhibit serine protease (coagulation factor) in the clotting cascade, have large individual difference in pharmacodynamics and complex pharmacodynamic-affecting factors, and therefore their clinical application requires to be monitored continuously. For decades, the major approach and one of the goals of anticoagulant development is to improve the selectivity of new drugs for a particular pharmacological target, improve the pharmacodynamic and pharmacokinetic characteristics of the drugs. The studies have made positive progress, among which the most representative is the clinical application of low-molecular-weight heparin (LMWH) such as enoxaparin and oral anticoagulants such as Rivaroxaban and Dabigatran. However, there is still a huge demand in clinic for new anticoagulants with low bleeding tendency.

Fucosylated glycosaminoglycan (FGAG) is a glycosaminoglycan analogue from the body wall or viscera of an echinoderm of Holothuroidea: FGAG has a chondroitin sulfate-like backbone, and the backbone is constituted by sequential connection of disaccharide structural units consisting of hexuronic acid, hexosamine ([→4) D-GlcUA (β1→3) D-GalNAc (β1→]); the backbone chain of FGAG has fucosyl side chains. Generally, it is considered that the sulfated fucoseside chain is linked to D-GlcUAvia a glycosidic bond; both the hydroxyl groups on the backbone chain and side chain of FGAG may have sulfation (Yoshida et. al, *Tetrahedron Lett*, 1992, 33: 4959-4962; Mourão et. al, *J Biol Chem*, 1996, 271: 23973-23984).

All native FGAG exhibits significant anticoagulant activity (Mourão et al., *Thromb Res*, 2001, 102: 167-176; Mourão et. al, *J Biol Chem*, 1996, 271: 23973-23984) and the anticoagulant activity involves multiple coagulation factor targets, among which the inhibitory activity for the intrinsic factor Xase (f.Xase, Tenase) is the strongest (Sheehan & Walke, *Blood*, 2006, 107:3876-3882; Buyue & Sheehan, *Blood*, 2009, 114: 3092-3100). Besides the anticoagulant activity, FGAG also has wide pharmacological activities, such as anti-inflammatory, anti-tumor, fibrinolysis, blood lipid-regulating activity (Tovar et al., *Atherosclerosis*, 1996, 126:185-195; Kariya et al., J Biochem, 2002, 132(2):335-343; Borsig et al., *J Biol Chem*, 2007, 282(20): 14984-14991), and shows platelet activation and f.XII activation that are contradictory to its anticoagulant activity (Li et al., *Thromb Haemost*, 1988, 59(3):435-439; Fonseca et al., *Thromb Haemost*, 2010, 103(5): 994-1004). The wide pharmacological activities limit the practical application of FGAG.

Structural modification of FGAG is one of approaches to improve its potential application value, for example, preparation of its depolymerized products, the purpose is to decrease the activities of platelet and contact activation, while maintaining the anticoagulant activity. Chinese Patent Publication Nos. CN101724086A and CN101735336A disclose a method for preparing depolymerized fucosylated glycosaminoglycan, wherein the depolymerized product is prepared by peroxide depolymerization that is catalyzed with transition metal ion of the fourth period in an aqueous medium. The product is a potent inhibitor of intrinsic factor Xase, having good anticoagulant and antithrombotic activities, significantly reduces bleeding tendency, and can be used for the prevention and/or treatment of thrombotic diseases. European patents EP 0811635A1 and EP 0408770A1 obtain depolymerized products having a molecular weight of 3,000-80,000 and 3,000-42,000, respectively, by hydrogen peroxide depolymerization of native FGAG. The products can be used in the prevention and treatment of vascular intimal hyperplasia and thrombosis diseases. All of those patent applications employ peroxide depolymerization to obtain depolymerized products of FGAG. The advantage of peroxide depolymerization is that while the molecular weight of the polysaccharide is reduced, the characteristic chemical structure and anticoagulant activity of FGAG can also be well maintained. The disadvantage is that the depolymerization degree of the product is difficult to control, and it is generally required to detect the reaction products by continuous sampling, so as to confirm whether the reaction is complete. Hitherto, the fucosylated glycosaminoglycan derivative having $\Delta^{4,5}$ unsaturated bonds at non-reducing terminal has not been reported yet.

SUMMARY OF THE INVENTION

The object of the present invention is to provide a derivative of low-molecular-weight fucosylated glycosaminoglycan (dLFG) having anticoagulant activity, a preparation method thereof, a pharmaceutical composition comprising the dLFG or a pharmaceutically acceptable salt thereof, and the use of the dLFG and pharmaceutical compositions thereof in preparing medicine for treating thrombotic diseases.

In order to achieve the above object, the present invention provides the following technical solutions:

The present invention first provides a low-molecular-weight fucosylated glycosaminoglycan derivative (dLFG) and a pharmaceutically acceptable salt thereof. The monosaccharide compositions of dLFG comprise hexuronic acid, hexosamine, deoxyhexamethylose and the sulfated forms thereof. Wherein, the hexuronic acid is D-glucuronic acid (D-GlcUA) and $\Delta^{4,5}$-hexuronic acid (4-deoxy-threo-hex-4-enepyranosyl uronic acid, $\Delta$UA), and the hexosamine is D-acetylgalactosamine (2-N-acetyl amino-2-deoxy-D-galactose, D-GalNAc) or a terminal reduction product thereof, the deoxyhexamethylose is L-fucose (L-Fuc).

Based on molar ratio, the ratio of each monosaccharide and $-OSO_3^-$ of the dLFG is hexuronic acid:hexosamine:deoxyhexamethylose:sulfate=1:(1±0.3):(1±0.3):(3.0±1.0). Generally, in the hexuronic acid of the dLFG of the present invention, the percentage of $\Delta$UA is not less than 2.5% based on molar ratio.

The molecular weight of the dLFG in the present invention can be determined and calibrated by online high performance gel permeation chromatograph with low angle laser light scattering instrument (HPGPC-LALLS); Series dLFG with calibrated molecular weights were used as standard samples to make standard curve; the molecular weight of the dLFG can be routinely determined by high performance gel permeation chromatograph in combination with UV detector (UVD) and/or refractive index detector (RID).

Based on weight average molecular weight (Mw), the dLFG of the present invention has a molecular weight of 3 kD-20 kD; in a preferred embodiment of the present invention, the dLFG has a molecular weight of about 5 kD-12 kD.

Generally, the dLFG of the present invention has a polydispersity index (PDI) of between 1.0 and 1.8. The PDI refers to the ratio of weight average molecular weight (Mw) to number average molecular weight (Mn) of the dLFG. In a preferred embodiment of the present invention, the dLFG has a PDI of between 1.1 and 1.5.

Further, the low-molecular-weight fucosylated glycosaminoglycan derivative of the present invention is a mixture of the homologous glycosaminoglycan derivatives having a structure of Formula (I),

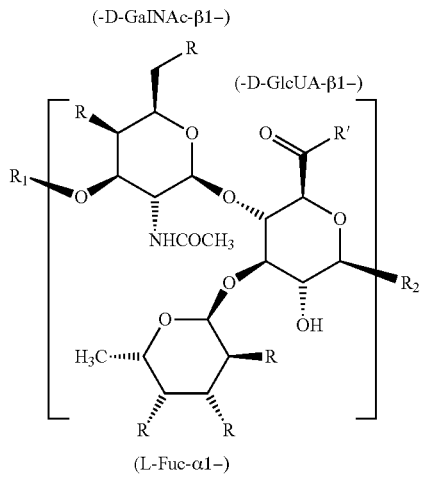

in Formula (I):

n is an integer with average value of about 2-20; in preferred compounds of the present invention, n is an integer with average value of about 4-12;

-D-GlcUA-β1- is -D-glucuronic acid-β1-yl;

-D-GalNAc-β1- is -2-deoxy-2-N-acetylamino-D-galactose-β1-yl;

L-Fuc-α1- is -L-fucose-α1-yl;

R independently is —H or —SO$_3^-$;

R' is —OH, C1-C6 alkoxy or C7-C12 aryloxy;

$R_1$ is a non-reducing terminal of the homologous glycosaminoglycan derivatives, the structure of which is a group shown in Formula (II) or (III),

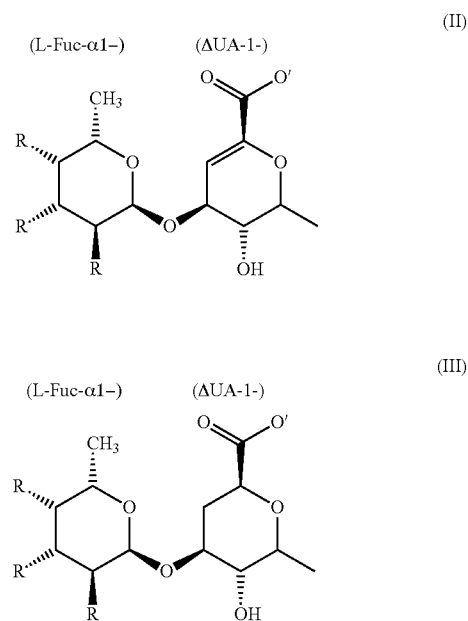

in Formula (II), (III), $\Delta$UA-1- is $\Delta^{4,5}$-hexuronic acid-1-yl (4-deoxy-threo-hex-4-enepyranosyluronic acid-1-yl);

R, R' are defined as above.

In the mixture of homologous glycosaminoglycan derivatives of the present invention, based on molar ratio, the ratio of the compounds that $R_1$ is Formula (II) to the compounds that $R_1$ is Formula (III) is not less than 2:1. In a preferred embodiment of the present invention, in the mixture of homologous glycosaminoglycan derivatives, the molar ratio of the non-reducing terminal $R_1$ being Formula (II) to $R_1$ being Formula (III) is not less than 4:1.

$R_2$ is a group shown in Formula (IV) or (V),

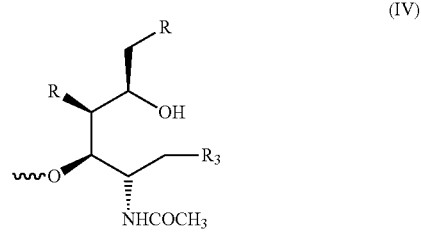

(V)

wherein, R, R' are defined as above;

$R_3$ is carbonyl, hydroxyl, C1-C6 alkoxy, C1-C6 carbalkoxy, C6-C12 aryl, substituted or non-substituted five or six-membered nitrogen-containing heterocyclic group, or —$NHR_4$; wherein, $R_4$ in —$NHR_4$ is substituted or non-substituted straight or branched chain C1-C6 alkyl, substituted or non-substituted C7-C12 aryl, substituted or non-substituted heteroatom-containing heterocyclic aryl.

In a preferred embodiment of the present invention, $R_3$ is —CHO or —$CH_2OH$.

The dLFG of the present invention is a depolymerized product obtained by β-elimination of fucosylated glycosaminoglycan (FGAG) extracted from body wall and/or viscera of an echinoderm of the class Holothuroidea, and a product obtained by reduction or reductive amination of the reducing terminal of the FGAG depolymerized product. The FGAG from the echinoderm generally has the following characteristics:

(1) The FGAG is extracted from the body wall and/or viscera of an echinoderm of the class Holothuroidea, and the extraction method is well known by the person skilled in this art, and also can be found in the references, for example, Yoshida et. al., *Tetrahedron Lett*, 1992, 33: 4959-4962; Mourão et. al., *J Biol Chem*, 1996, 271: 23973-23984; Mourão et al., *Thromb Res*, 2001, 102: 167-176; Mourão et. al, *J Biol Chem*, 1996, 271: 23973-23984; Tovar et al., *Atherosclerosis*, 1996, 126: 185-195; Kariya et al., *J Biochem*, 2002, 132(2): 335-343; Borsig et al., *J Biol Chem*, 2007, 282(20): 14984-14991.

(2) The monosaccharide compositions of FGAG comprise D-glucuronic acid (GlcUA), D-N-acetyl-2-amino-2-deoxygalactose (GalNAc) and L-fucose (Fuc), and these monosaccharide components may have sulfate substituents;

(3) The backbone chain of FGAG comprises a repeated structural unit of [-4-D-GlcUA-β1-3-D-GalNAc-β1-], Fuc as a side chain is linked to GlcUA of the main chain.

Generally, the FGAG has a structure shown in Formula (VI):

(VI)

in Formula VI,
n is an integer with average value of about 40-90;
R independently is —OH or —$OSO_3^-$;
$R_5$ is —H or D-GlcUA-β1-;
$R_6$ is —OH, -4-D-GalNAc or sulfate thereof.

The echinoderm of the class Holothuroidea of the present invention includes but not limited to:

*Apostichopusjaponicus;*
*Actinopygamauritiana;*
*Actinopygamiliaris;*
*Acaudinamolpadioides;*
*Bohadschiaargus;*
*Holothuriaedulis;*
*Holothurianobilis;*
*Holothurialeucospilota;*
*Holothuriasinica;*
*Holothuriavagabunda;*
*Isostichopusbadionotus;*
*Ludwigothureagrisea;*
*Stichopuschloronotus;*
*Thelenotaananas;*
*Thelenotaanax.*

In a preferred embodiment of the present invention, the echinoderm of the class Holothuroidea may include *Apostichopus japonicas, Holothurialeucospilota* and *Thelenotaananas*.

Another object of the present invention is to provide a preparation method of the dLFG and a pharmaceutically acceptable salt thereof. The preparation method generally comprises the following steps of:

(1) using fucosylated glycosaminoglycan (FGAG) from an echinoderm as raw material, subjecting it to esterification reaction to totally or partially convert free carboxylic groups of GlcUA in FGAG into carboxylate groups, to obtain an esterification derivative of FGAG;

(2) subjecting the esterification derivative of FGAG obtained in step (1) to β-elimination reaction, in a non-aqueous solvent, in the presence of a basic reagent, to obtain a low-molecular-weight glycosaminoglycan derivative (dLFG) having non-reducing terminal $\Delta^{4,5}$-hexuronic acid (ΔUA);

(3) subjecting the dLFG obtained in step (2) to optional reduction treatment at the reducing terminal, to obtain a terminal-reduced dLFG;

(4) subjecting the dLFG obtained in step (2) and step (3) to optional basic hydrolysis to convert the carboxylate groups and/or amide groups into free carboxyl groups.

The inventors have found that native fucosylated glycosaminoglycan (FGAG) is relatively stable in basic aqueous solution; however, under drastic reaction conditions such as elevated temperature and enhanced alkalinity, the β-elimination reaction of FGAG may be accompanied by the destruction of the characteristic structures of the FGAG, including hydrolysis of fucosylated side chains, backbone structure and sulfate esters, so it is difficult to predict the reaction products, and chemical structure of products are very complex and difficult to be confirmed. Obviously, it is difficult to obtain FGAG depolymerized products with homogeneous structure by direct treatment with an alkali.

In order to achieve the depolymerization of FGAG by β-elimination, the present invention establishes a depolymerization method by selective esterification of free carboxyl groups of hexuronic acid, followed by β-elimination that is performed under mild conditions and can retain complete characteristic structure of FGAG. In the present invention, the "complete characteristic structure" refers to: except that the molecular weight is decreased and the terminals (including reducing terminal and non-reducing terminal) may be chemically modified, the basic chemical structural characteristics of the depolymerized products are identical to that of the non-depolymerized polysaccharide, including monosaccharide compositions and their relative molar ratio, linkage types of repeating structure units, number and type of sulfate groups.

In the present invention, the preparation method of a carboxyl esterification product of FGAG comprises:

(1) converting FGAG into quaternary ammonium salt by ion exchange method, for example, converting neutral FGAG salt to $H^+$ type FGAG by $H^+$ type cation exchange resin;

(2) titrating/neutralizing the obtained $H^+$ type FGAG solution with quaternary ammonium hydroxide solution, to obtain FGAG quaternary ammonium salt solution, which is lyophilized to obtain FGAG quaternary ammonium salt. The quaternary ammonium hydroxide may include but not limited to tetrabutylammonium hydroxide, dodecyl trimethyl ammonium hydroxide, tetramethyl ammonium hydroxide, tetrapropyl ammonium hydroxide, tetraethyl ammonium hydroxide, benzyl trimethyl ammonium hydroxide and benzyl triethyl ammonium hydroxide.

(3) reacting FGAG quaternary ammonium salt with stoichiometric alkyl halides in a non-protonic solvent such as N,N-dimethylformamide (DMF), subjecting the reaction product to isolation and purification to obtain FGAG carboxylate derivative (the quaternary ammonium salt, which can be directly used for further β-elimination reaction). Alkyl groups of the alkyl halides include but not limited to, C1-C6 straight or branched chain, saturated or unsaturated, substituted or unsubstituted aliphatic hydrocarbon group, substituted or unsubstituted C7-C12 aromatic hydrocarbon group, etc.

Another patent application with an application number 201110318704.X (publication number CN102329397A) of the present applicant discloses a method of preparing FGAG carboxylate derivatives.

During the preparation of low-molecular-weight heparin (LMWH), carboxylate derivatives of unfractionated heparin can perform β-elimination reaction in aqueous basic solution, thus can produce low-molecular-weight heparin (LMWH) containing terminal ΔUA. The present inventors have been surprised to found from experimental studies that under similar conditions such as NaOH aqueous solution, the carboxyl esterification product of FGAG can be hydrolyzed completely into native FGAG, with little or almost without β-elimination reaction. Therefore, the present invention has focused on non-aqueous solvent system for performing β-elimination reaction of carboxylate derivatives of FGAG.

In the preparation method of dLFG and a pharmaceutically acceptable salt thereof as mentioned above, the non-aqueous solvent in step (2) is optionally selected from ethanol, methanol, dimethylformamide, dimethylsulphoxide, $CH_2Cl_2$, $CHCl_3$ or a mixture thereof. The basic reagent is optionally selected from NaOH, KOH, C1-C4 sodium alcoholate, ethylenediamine, tributylamine, 4-dimethylamino pyridine, 1,8-diazabicyclo[5.4.0]undec-7-ene or a mixture thereof.

When β-elimination reaction of the FGAG carboxylate derivative is performed in a non-aqueous solvent, the key technical difficulty to be resolved is that the solubility of FGAG carboxylate derivative is very poor in the non-aqueous solvent, which seriously affects the performance of the desirable β-elimination. The present invention improves the solubility of FGAG carboxylate derivative in non-aqueous solvent by converting it into a quaternary ammonium salt, and thus achieves a desirable solubility of the FGAG carboxylate derivative in non-aqueous solvent that can meet the requirement of β-elimination reaction.

When a single lower alcohol or ketone such as ethanol is used as solvent, the quaternary ammonium salt of the FGAG carboxylate derivative has a relatively low solubility; and when other non-aqueous solvents such as N,N-dimethylformamide (DMF) are used, the reaction efficiency is largely limited, because NaOH that is used as a catalyst has a very low solubility. Therefore, in the schemes of the present invention, on one hand, C1-C4 sodium alcoholate is used as an alkaline reagent to improve the concentration of the alkaline reagent in the non-aqueous solvent; on the other hand, a mixture solvent system is used as a solvent system of β-elimination reaction. The reaction system is performed by the following steps: dissolving the quaternary ammonium salt of FGAG carboxylate derivative in a non-aqueous solvent such as DMF; dissolving NaOH or other suitable base catalyst in an anhydrous lower alcohol; mixing the quaternary ammonium salt solution of FGAG carboxylate derivative and the base catalyst solution, to obtain a clear β-elimination reaction system.

The alkaline reagent includes but not limited to: NaOH, KOH, C1-C4 alcohol sodium, ethylenediamine, tributylamine, 4-dimethylamino pyridine, 1,8-diazabicyclo[5.4.0]undec-7-ene or a mixture thereof. The preferred alkaline reagent of the present invention is sodium ethoxide. The preferred technical method comprises adding stoichiometric metal sodium into anhydrous ethanol to obtain sodium ethoxide-ethanol solution.

In said β-elimination reaction solution, the concentration of the quaternary ammonium salt of FGAG carboxylate derivative is generally 1-150 mg/ml, and the concentration of the alkaline catalyst is generally 0.1-100 mmol/L. In the β-elimination reaction solution, the β-elimination reaction of the FGAG carboxylate product can be well carried out, and generally the reaction is complete after reacting at room temperature for 0.1-8 h. After completion of the β-elimination reaction, the reaction solution is neutralized with an acid (such as hydrochloric acid) to obtain carboxylate product of dLFG; alternatively, without changing the alkaline condition of the reaction solution, proper amount of water is added to the reaction solution and maintained for 0.5-1 h at room temperature, so as to completely hydrolyze the carboxylate groups of the depolymerized dLFG derivative. Then, dLFG product containing free carboxyl groups can be obtained by neutralizing the reaction solution with an acid.

Generally speaking, the preparation of FGAG carboxylate and β-elimination depolymerization may comprise:

The neutral salt of FGAG is subjected to H+ cation exchange resin column and neutralized by titrating with quaternary ammonium hydroxide to obtain FGAG quaternary ammonium salt, and then reacted with alkyl halide in non-protonic solvent under room temperature or heat condition (carboxyl esterification) to obtain FGAG carboxylate product (quaternary ammonium salt), and then it is dissolved in a non-aqueous solvent, added with a strong base, reacted under room temperature or heat condition (β-elimination) to finally obtain dLFG (depolymerized product of FGAG by β-elimination).

In theory, when the carboxyl esterification degree of FGAG is about 5%-30%, and is depolymerized according to the β-elimination method of the invention, the product obtained may have a molecular weight of about 3 kD-20 kD. In the actual reaction, given the effect of experimental condition on the β-elimination reaction degree, FGAG carboxylate product having a carboxyl esterification rate of about 10%-60% is used for the β-elimination depolymerization, and the obtained dLFG product has a Mw of about 3 kD-20 kD.

The dLFG obtained from β-elimination of the invention has a reducing terminal, and the reducing terminal is mainly -4-D-N-acetyl-2-amino-2-deoxygalactose (-4-D-GalNAc). In the present invention, the reducing terminal can be modified by optional reduction reaction. The reduction reaction may include but is not limited to:

(1) reducing the reducing terminal into a alditol in the presence of a reducing agent such as sodium borohydride. Taking -4-D-N-acetyl-2-amino-2-deoxygalactose as an example, the reaction route is:

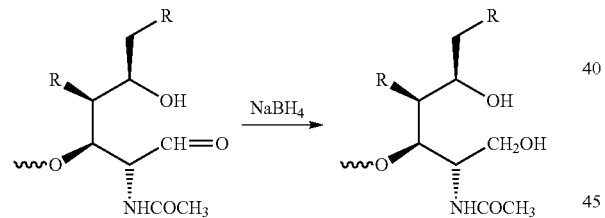

wherein, R is —OH or —OSO$_3^-$.

(2) subjecting the reducing terminal to reductive amination in the presence of an organic amine; comprising reacting the organic amine with 1-aldehyde group of the terminal glycosyl to produce a Schiff base, which is reduced in the presence of a reducing agent, to produce a secondary amine. Taking the reaction of terminal -4-D-N-acetyl-2-amino-2-deoxygalactose and ammonium bicarbonate and primary amine as an example, the reaction route is:

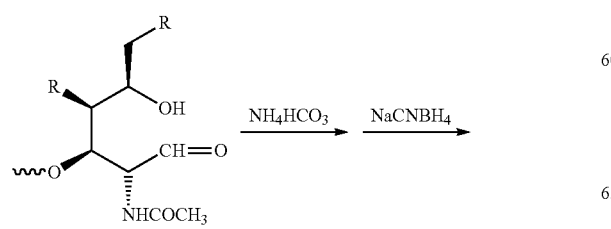

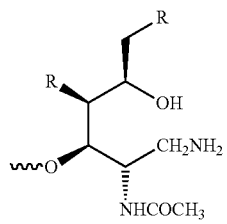

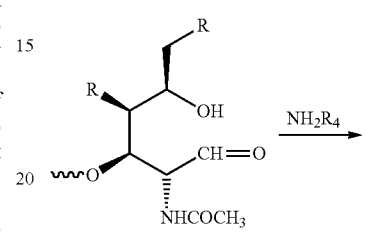

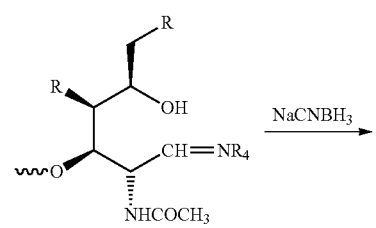

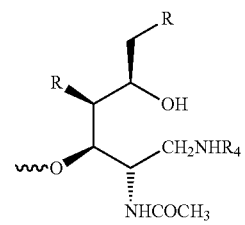

wherein, R$_4$ is H, substituted or non-substituted straight or branched chain C1-C6 alkyl, substituted or non-substituted C7-C12 aryl, substituted or non-substituted heteroatom-containing heterocyclic aryl. The heteroatom includes but is not limited to O, N, S.

(3) in the presence of a reducing compound, subjecting the reducing terminal to reductive alkylation to obtain a reductive alkylation derivative. Taking the reaction of terminal -4-D-N-acetyl-2-amino-2-deoxygalactose with a reducing agent such as pyrazolone compound as an example, the reaction route is:

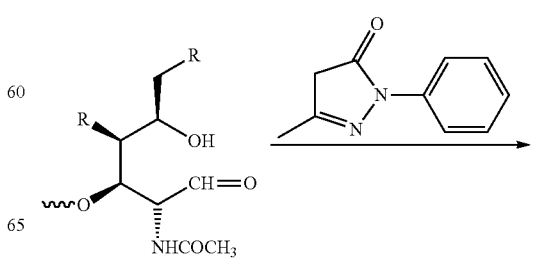

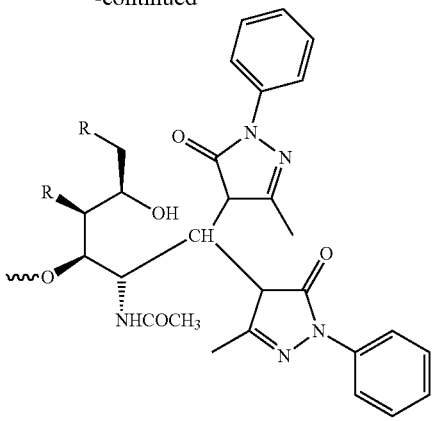

Reduction reaction of reducing terminal of an aldose, reductive amination reaction and reductive alkylation reaction are well known by the person skilled in this art. In the present invention, when the dLFG obtained from β-elimination is subjected to reductive reaction at the reducing terminal, a terminal glycosyl shown in Formula (IV) and (V) can be obtained, wherein $R_3$ is C1-C6 alkoxy, C1-C6 alkoxy carbonyl, C6-C12 aryl, substituted or non-substituted five or six-membered nitrogen-containing heterocyclic group, or —$NHR_4$ ($R_4$ is substituted or non-substituted straight or branched chain C1-C6 alkyl, substituted or non-substituted C7-C12 aryl, substituted or non-substituted heteroatom-containing heterocyclic aryl).

The reaction product dLFG of the present invention can be purified according to the known methods in the art (Chinese patent publication No. CN101735336A), for example, dialysis or ultrafiltration method may be used to remove small molecule salts and other impurities, or gel chromatography and DEAE ion exchange chromatography may be used for further purification.

In the process of dialysis for impurity removal, the dialysis membrane or ultrafiltration membrane with suitable molecular weight cutoff may be selected according to the molecular weight of the target compound dLFG. Preferably, the molecular weight cutoff is 1000 Da. The dialysis time should be determined according to the specific processing conditions, usually not less than 6 hours.

The dLFG product of the invention may also be prepared into a single salt form by cation exchange, such as alkali metal, alkaline earth metal and organic ammonium salt. In a preferred embodiment of the invention, a single salt form of the dLFG is sodium salt, potassium salt or calcium salt.

The salt-forming process of the dLFG product may comprise first exchanging the sample into hydrogen type, then neutralizing it with an alkali to obtain the corresponding salt of the dLFG; or preferably exchanging it into a salt on the column directly by dynamic ion exchange method, wherein strongly acidic cation exchange resin may be used. Resin column pretreatment, sample loading and elution may be carried out according to conventional methods.

The dLFG of the invention is prepared by β-elimination reaction using FGAG from an echinoderm as raw material. As mentioned above, in the present invention, the source of the raw material FGAG may be selected from the group consisting of but not limited to *Apostichopus japonicas, Actinopygamauritiana, Actinopygamiliaris, Acaudinamolpadioides, Bohadschiaargus, Holothuriaedulis, Holothurianobilis, Holothurialeucospilota, Holothuriasinica, Holothuriavagabunda, Isostichopusbadionotus, Ludwigothureagrisea, Stichopuschloronotus, Thelenotaananas, Thelenotaanax*. In a preferred embodiment of the invention, the source includes *Apostichopus japonicas, Holothurianobilis* and *Thelenotaananas*.

The structure characteristic of FGAG from an echinoderm of the class Holothuroidea of the invention is: the molar ratio of GlcUA:GalNAc:fucose is about 1:(1±0.3):(1±0.3). Different holothurian species, different tissue sources or different extraction methods may lead to FGAG having different monosaccharide component ratios and polysaccharide sulfation degrees. These differences do not influence the basic structure characteristic of FGAG. Obviously, the ordinary person skilled in the art can understand that the fucosylated glycosaminoglycan from other holothurian species and with the basic structure characteristic of FGAG can be used for preparing the dLFG derivative of the present invention.

The dLFG of the present invention has potent anticoagulant activity, and its drug concentration that is required for doubling the activated partial thromboplast time (APTT) of human control plasma (the concentration that doubles APTT) is not more than 9 μg/mL. The studies of the present invention confirm that the dLFG has a potent activity of inhibiting intrinsic factor Xase (f.Xase, Tenase), and has heparin cofactor II (HC-II)-dependent anti-thrombin (f.IIa) activity. Since factor Xase is the last enzymatic site in the intrinsic coagulation pathway, and is the rate limiting site of multiply experimental coagulation process (Buyue & Sheehan, *Blood*, 2009, 114: 3092-3100). Dermatan sulfate having HC-II-dependent anti-thrombin (f.IIa) activity has been used for antithrombotic treatment in clinical; therefore, the dLFG has the potential application in clinical treatment for thromboembolic disease.

The dLFG of the invention has no platelet activating activity; in addition, the inventors have been surprised to find that, compared to native FGAG, the dLFG of the present invention has no f.XII activating activity and does not influence the f.XII-kallikrein system and will not lead to reduced blood pressure in experimental animals.

The non-reducing terminal of the dLFG of the present invention may have ΔUA glycosyl, and the unsaturated double bonds of ΔUA allow it to have maximum UV absorption (UV, $\lambda_{max}$) at about 232-238 nm. This property is of great value for establishing a qualitative and quantitative analysis method based on UV spectrophotometric determination, especially when high performance liquid phase gel chromatography (HPGPC) is used for analyzing the dLFG content in the sample, a UV detector with high sensitivity can be used for the detection. Thus, it is especially suitable for establishing a technology method related to dLFG content analysis such as sample quality control, plasma-drug concentration analysis.

The dLFG of the present invention has definite anticoagulant activity and thus has antithrombotic application value. The dLFG has good solubility in water, thus, it can be easily prepared into a solution preparation or freeze-dried products. As a polysaccharide component, its oral bioavailability is limited, so it is preferably prepared into parenteral dosage forms and the preparation may be prepared according to the well-known technical methods in the art.

Therefore, another object of the present invention is to provide a pharmaceutical composition comprising the dLFG of the present invention and a pharmaceutically acceptable excipient.

The dLFG of the invention has a potent anticoagulant activity, and thus can be used for the prevention and treatment of different degrees of thrombotic diseases, such as thrombotic cardiovascular disease, thrombotic cerebrovascular disease, pulmonary venous thrombosis, peripheral venous thrombosis, deep venous thrombosis, and peripheral arterial thrombosis. Therefore, the invention also provides a use of the compositions for preparing medicine for the prevention and treatment of cardiovascular diseases.

The dLFG of the invention has a potent anticoagulant activity, and thus can be used for the prevention and treatment of different degrees of thrombotic diseases, such as thrombotic cardiovascular disease, thrombotic cerebrovascular disease, pulmonary venous thrombosis, peripheral venous thrombosis, deep venous thrombosis, and peripheral arterial thrombosis. Therefore, the invention also provides a use of the compositions for preparing medicine for the prevention and treatment of cardiovascular diseases.

The present invention studies and establishes a β-elimination depolymerization method firstly. It is found from the studies that native FGAG is relatively stable in basic solution, and β-elimination is not easy to occur. Carboxyl esterification followed by β-elimination is an alternative technical method, but since there are fucosyl side chain substituents in FGAG, the polysaccharide structure is more complex. On one hand, the complex steric hindrance may influence chemical reaction properties of a variety of chemical functional groups; on the other hand, many chemical reaction conditions can affect the stability of glycosidic bonds of the fucosyl side chains. The inventors are surprised to find that unlike the heparin esterification product, the FGAG carboxylate product cannot perform a β-elimination reaction in alkaline aqueous solution. Actually, in alkaline aqueous solution, the ester groups of the FGAG carboxylate product are prone to be hydrolyzed, almost without performing β-elimination reaction, which is very different to the property of the typical glycosaminoglycan compounds such as heparin.

By β-elimination reaction of FGAG carboxylate products in non-aqueous solvent, the present invention successfully obtains the fucosylated glycosaminoglycan depolymerized products having $\Delta^{4,5}$ unsaturated bonds at non-reducing terminals.

Fucosylated glycosaminoglycan derivatives (dLFG) with desirable molecular weight range can be obtained by the technical method of the present invention. The analysis of physicochemical properties and spectroscopy shows that except that there are $\Delta^{4,5}$ unsaturated bonds at reducing terminals, the basic structure retains stable.

When LFG is prepared by the method of the present invention, the molecular weight of the reaction product can be effectively controlled by controlling the ratio of carboxyl esterification and/or amidation; Since there are $\Delta^{4,5}$ unsaturated bonds at non reducing terminals of the product, the obtained dLFG has maximal UV absorption at about 232-240 nm ($\lambda_{max}$), and this property can be used for quantitative detection of the product, it is conducive to the establishment of technical methods that are related to content analysis, such as chemical reaction control, product quality analysis and plasma-drug concentration detection.

The results of pharmacological experiments show that the dLFG prepared by the method of the invention has significant anticoagulant activity, the activity of prolonging activated partial thromboplastin time (APTT) of human control plasma, the activity of inhibiting intrinsic factor Xase (f.Xase, Tenase) and heparin cofactor II (HC-II)-dependent anti-thrombin (anti-f.XIIa) activity are substantially identical to that of the peroxide depolymerized product with similar molecular weight, which indicates that it has good potential application value. Compared to the peroxide depolymerized product, the dLFG of the present invention has the advantages that: first, it has non-reducing terminals with specific structure, has the ultraviolet absorption with $\lambda_{max}$ at about 232-240 nm, and the quality controllability is significantly improved; second, the preparation process has good controllability.

Further studies of the present invention found that, the dLFG of the invention do not have the activities of platelet and factor XII (f.XII) activation under the effective anticoagulant dose, and thus can avoid series of adverse effects induced by platelet activation and f.XII-kallikrein system activation. Compared to the equivalent antithrombotic dose of heparin, the low-molecular-weight FGAG of the present invention can further decrease bleeding tendency, and has the value for treating and/or preventing thrombotic diseases.

DESCRIPTION OF THE DRAWINGS

FIG. 12 shows basic route of β-elimination depolymerization of FGAG

DETAILED DESCRIPTION OF THE INVENTION

Figure 1:
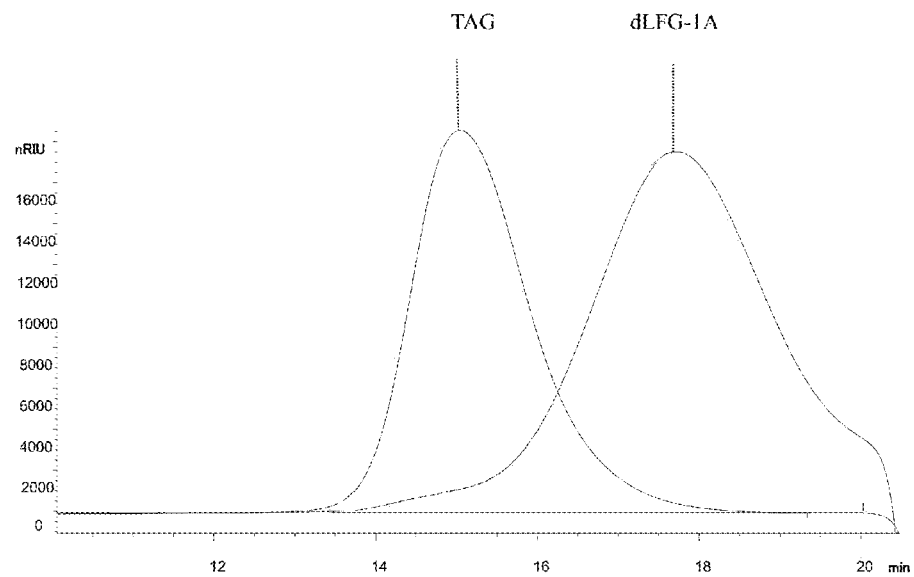
FIG. 1 shows HPGPC chromatogram of TAG and dLFG-1A.

The following examples are used to illustrate the substantive content of the present invention in detail in conjunction with the drawings, but not intended to limit the scope of the invention in any way.

Example 1

Preparation of Low-Molecular-Weight Fucosylated Glycosaminoglycan Derivative (dLFG) from *Thelenotaananas*

1.1 Materials

*Thelenotaananas* Jaeger, commercially available, dry body wall without viscera; Reagents such as benzethonium chloride, benzyl chloride, tetrabutyl hydroxide ammonium (TBA), N,N-dimethylformamide (DMF), sodium hydroxide, sodium chloride and ethanol were commercially available analytical pure reagents.

1.2 Methods (1) Extraction and Preparation of FGAG from *Thelenotaananas* (TAG):

300 g of dry body wall of *Thelenotaananas* was used to prepare TAG, according to the method of the reference (Kariya et al., *J Biol Chem*, 1990, 265(9):5081-5085). Yield:

about 1.5%, Purity: 98% (HPGPC, area normalization method); weight-average molecular weight (Mw): 65,890 Da.

(2) Preparation of Quaternary Ammonium Salt of TAG:

1.2 g of TAG obtained in step (1) was placed in the flask and dissolved in 40 mL of deionized water; titrated with 75 mg/mL benzethonium chloride under stirring, and there were white precipitation in the solution immediately. After titration, the solution was centrifuged, and then the precipitation was washed with deionized water for three times and finally dried under vacuum at room temperature for 24 h, to obtain 2.68 g of FGAG ammonium salt.

(3) Preparation of TAG Benzyl Esters:

The quaternary ammonium salt of TAG obtained in step (2) was placed in a round-bottom flask, dissolved with 27 mL of DMF, added with 13.5 mL of benzyl chloride, and then reacted at 35° C. for 25 h under stirring, under the protection of $N_2$. After completion of the reaction, the reaction solution was added with 35 mL of saturated NaCl followed by 300 mL of anhydrous ethanol, and centrifuged at 3500 rpm for 20 min. The supernatant was removed. The precipitation was washed with 200 mL of saturated NaCl-anhydrous ethanol (1:9, v/v) for three times, dissolved in 100 mL of deionized water, dialyzed through 3.5 kD dialysis bag for 24 h. The dialysate was concentrated and lyophilized to obtain FGAG benzyl esters. Esterification degree was determined as 72% by $^1$H-NMR.

(4) Preparation of Trabutylammonium Salt of the TAG Benzyl Esters:

The benzyl esters of TAG obtained in step (3) was dissolved in water, and converted to hydrogen type by ion exchange (Dowex/r50w×8 50-100(H), 60×3 cm), and then titrated with 0.4M tetrabutylammonium hydroxide ammonium solution under the monitoring of conductivity meter so as to completely convert the sulfate groups and remnant carboxyl groups of esterification into ammonium salts. The obtained solution was lyophilized to obtain 1.326 g of tetrabutylammonium salt of TAG benzyl esters.

(5) β-Elimination Depolymerization:

800 mg of tetrabutylammonium salt of TAG benzyl esters obtained in step (4) was dissolved in 8.0 mL of DMF, added with 0.8 mL of tributylamine, reacted at 60° C. for 24 h under stirring. Then the solution was added with 80 mL of saturated NaCl-anhydrous ethanol (1:9, v/v), centrifuged at 3500 rpm for 15 min to obtain precipitation. 8 mL of 0.1 M NaOH was added to the precipitation, reacted at 30° C. for 40 min to hydrolyze residual carboxylates. 0.1M HCl was used to adjust to neutral pH, and then 80 mL of ethanol was added, centrifuged at 3500 rpm for 15 min. The obtained precipitation was dissolved in 8 mL of $H_2O$, subjected to hydrogen type ion exchange resin column (Dowex/r50w×8 50-100(H), 60×3 cm), adjusted with 0.1M NaOH to neutral pH, dialyzed through 1 kD dialysis bag with deionized water for 24 h, lyophilized and obtained about 310 mg the β-elimination depolymerization product.

(6) Physicochemical Properties, Monosaccharide Compositions and Spectrum Detection of TAG and its β-Elimination Depolymerization Product (dLFG-1A)

Molecular weight: determined by high performance gel permeation chromatography (HPGPC). Chromatographic conditions: Agilent technologies 1200 series chromatography, ShodexOhpak SB-804 HQ gel permeation chromatography column, Column temperature: 35° C.; Mobile phase: 0.1M sodium chloride; Flow rate: 0.5 mL/min; Detection method: Agilent 1100 type RID-UVD. Standard curve was drawn with series FGAG with calibrated molecular weight. Molecular weight and distribution were calculated by GPC.

Molar ratio of $-OSO_3^-/-COO^-$: determined by conductometric method.

Optical rotation: determined according to the method of Chinese Pharmacopoeia (2010 edition) Volume II Appendix VIE;

Intrinsic viscosity: determined by Ubbelohde viscosity meter, according to the method of Chinese Pharmacopoeia (2010 edition) Volume II Appendix VIG.

Determination of monosaccharide compositions: The acetylgalactosamine (D-GalNAc) content was determined by Elson-Morgon method. The glucuronic acid (D-GlcUA) content was determined by carbazole method (Zhang weijie, Biochemical Research Technology of Glycoconjugate 2 Ed, Zhejiang: Zhejiang University Press, 1999, 19-20). The 4,5-unsaturated glucuronic acid residues (ΔUA) content was calculated according to the ratio of H4 integral to methyl in acetyl galactosamine (D-GalNAc) in $^1$H NMR. The NMR data were determined by Switzerland Bruker AVANCE AV 500 superconducting nuclear magnetic resonance instrument (500 MHz) (determination conditions: solvent $D_2O$, 99.9 Atom % D (Norell company); internal standard, trimethylsilyl-propionic acid (TSP-d4); temperature, 300 K).

Ultraviolet absorption spectrum (UV) detection: 0.855 mg/mL dLFG solution, scanned on Shimazu UV-2450 at 190-400 nm.

1.3 Results

The determination results of physicochemical properties and monosaccharide compositions of TAG and its depolymerized product (dLFG-1A) are shown in Table 1. The HPGPC chromatograms of TAG and dLFG-1A are shown in FIG. 1.

The determination results showed that the molecular weight and intrinsic viscosity of dLFG-1A were significantly decreased compared to TAG.

The determination results of monosaccharide compositions showed that the ratio of hexosamine, hexuronic acid (UA, the sum of GlcUA and ΔUA) and deoxyhexamethylose (Fuc) basically remained stable in TAG and dLFG-1A. It was known from the $^1$H NMR spectra mentioned hereinafter that there was no ΔUA in TAG, the molar ratio of ΔUA to GalNAc in dLFG-1A was about 0.18:1 (based on molar ratio, ΔUA was about 7.5% of the total hexuronic acid).

TABLE 1

Physicochemical properties and monosaccharide compositions of FGAG from *Thelenotaananas* and dLFG-1A

| Sample | Molecular weight (Mw) | PDI | Optical rotation ($[\alpha]_D^{20}$) | Intrinsic viscosity (0.1M NaCl) | Monosaccharide compositions (molar ratio) GalNAc:UA:Fuc:—$OSO_3^-$ |
|---|---|---|---|---|---|
| FGAG | 65,890 | 1.08 | −59.8° | 48.6 | 1.00:0.97:1.03:3.59 |
| dLFG-1A | 8,798 | 1.39 | −53.8° | 5.82 | 1.00:1.03:0.99:3.47 |

UV spectrophotometer was used to scan at a wavelength of 190 nm-400 nm. The dLFG has a maximum UV absorption ($\lambda_{max}$) at 236 nm, which conformed to the presence of unsaturated bonds in ΔUA.

Figure 2:
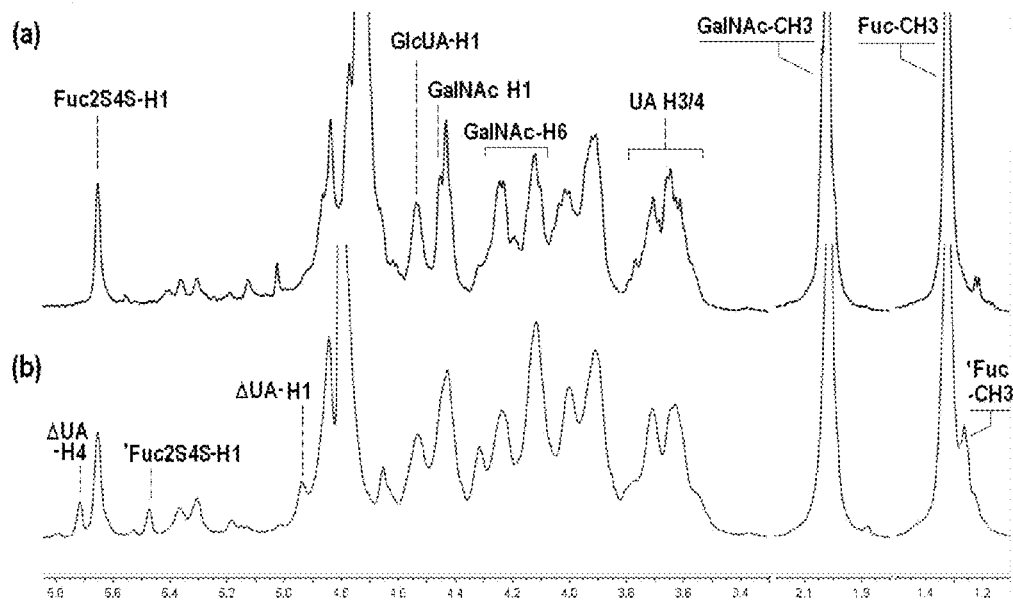
FIG. 2(a) shows $^1$H NMR spectrum of TAG.
FIG. 2(b) shows $^1$H NMR spectrum of dLFG-1A.
Figure 3:
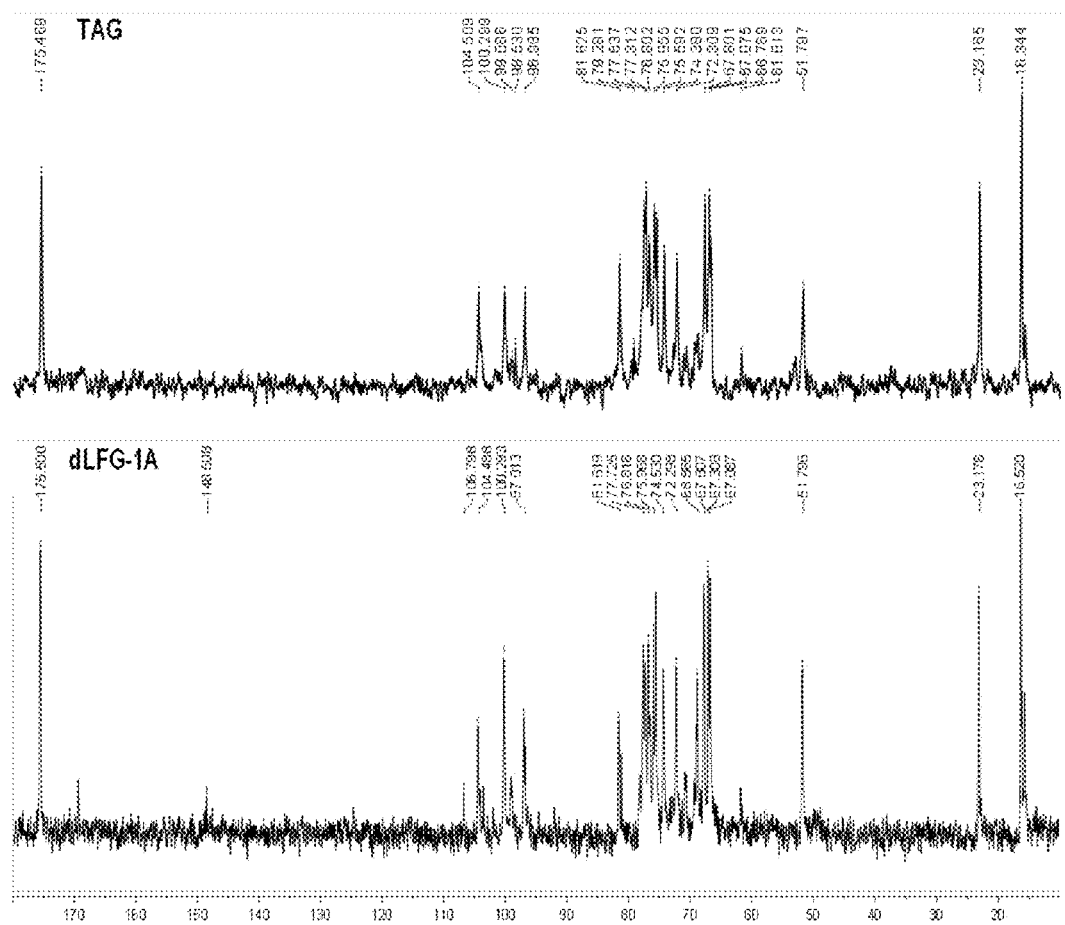
FIG. 3 shows $^{13}$C NMR spectra of TAG and dLFG-1A.
Figure 4:
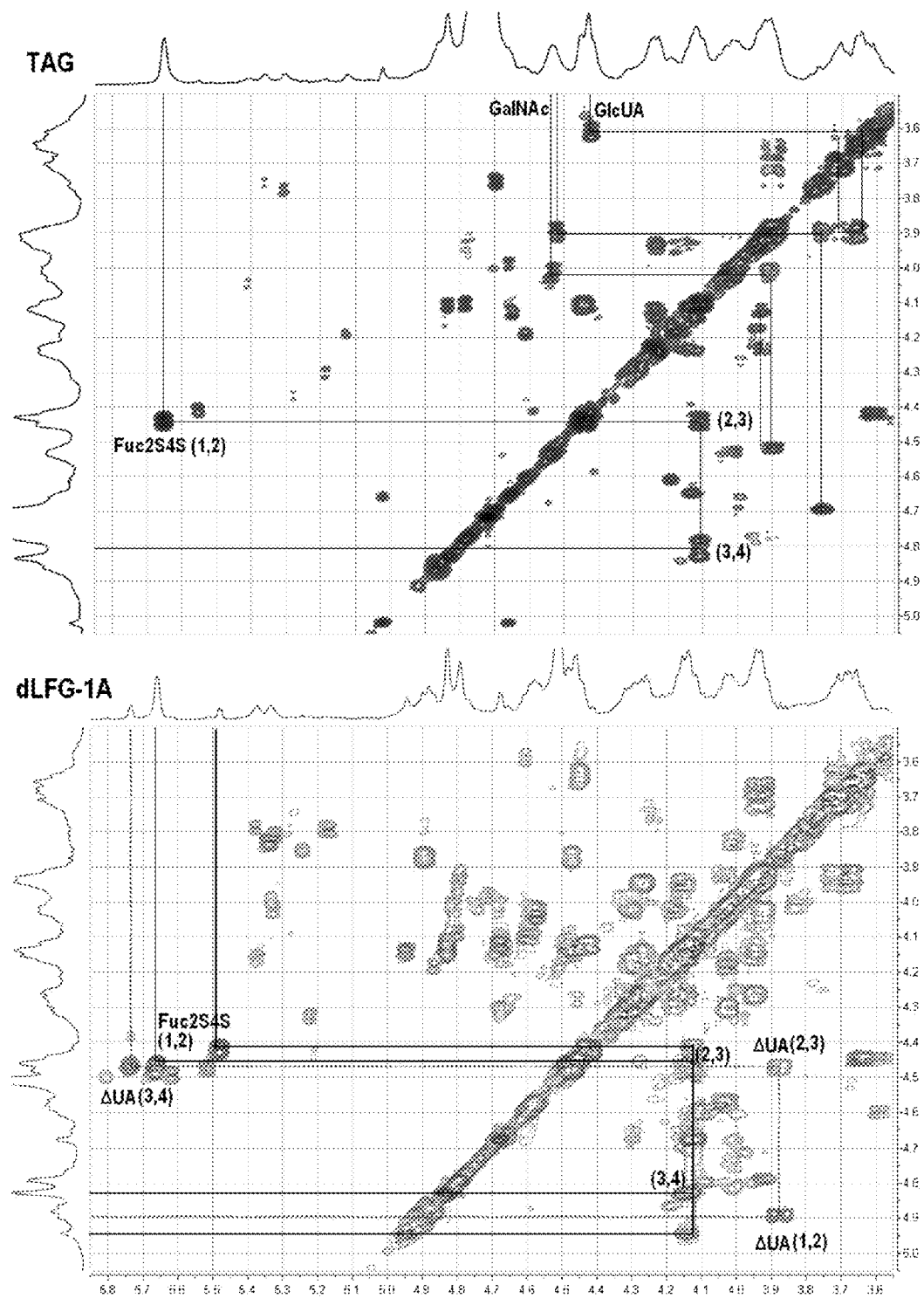
FIG. 4 shows $^1$H-$^1$H COSY NMR spectra of TAG and dLFG-1A.

In the present invention, FIG. 2 shows $^1$H NMR spectra of TAG and dLFG-1A; FIG. 3 shows $^{13}$C NMR spectra of TAG and dLFG-1A; FIG. 4 shows $^1$H-$^1$H COSY spectra of TAG and dLFG-1A; FIG. 5(a) shows $^1$H-$^1$H ROESY spectrum of TAG; FIG. 5(b) shows $^1$H-$^1$H TOCSY spectrum of TAG; FIG. 5(c) shows $^1$H-$^1$H ROESY spectrum of dLFG-1A; FIG. 5(d) shows $^1$H-$^1$H TOCSY spectrum of dLFG-1A; FIG. 6 shows $^1$H-$^{13}$C HSQC spectrum of dLFG-1A.

The signal assignment of $^1$H NMR and correlation spectra of TAG can refer to Chinese patent publication No. CN102247401A filed by the present applicant.

In the $^1$HNMR spectrum of TAG, there were three relatively strong signal peaks in the range of 5.2-5.7 ppm, which were assigned to anomeric protons of different types of sulfated α-fucose, wherein the signal at about 5.6 ppm was signal of anomeric proton of 2,4-O-disulfatedfucose (Fuc2S4S), the signal peaks at about 5.30-5.39 ppm were anomeric proton signals of 3-O-sulfatedfucose (Fuc3S) and 4-O-sulfatedfucose (Fuc4S).

The β-anomeric proton signals of main chain GlcUA and GalNAc were at about 4.4-4.6 ppm. At about 1.0-1.3 ppm and 1.9-2.0 ppm were methyl proton peaks of Fuc and acetyl of GalNAc, respectively. The saccharide ring hydrogen signals at the sulfate-substituted positions were present at 4.2-4.8 ppm, and the signals at 3.6-4.6 ppm were the superposition of hydrogens at the non-sulfate-substituted positions.

Compared to the spectra of TAG, there were new signals at 5.76 and 5.82 ppm in $^1$H NMR spectrum of dLFG-1A. According to correlation spectra, these signals can be assigned as the H4 of ΔUA.

The $^1$H-$^1$HCOSY spectrum and TOCSY spectrum of dLFG-1A clearly illustrated the coupling correlation between the proton signals of H4, H3, H2 and H1 of ΔUA. The $^1$H-$^1$H ROESY spectrum showed that Fuc was linked to GlcUA and ΔUA via α(1→3) glycosidic bond. In addition, compared to the anomeric proton signals of Fuc linked to GlcUA, the anomeric proton signals of the same kind of Fuc linked to ΔUA were present in higher field (See the signal positions of anomeric proton of Fuc2S4S and anomeric proton of Fuc2S4S linked to ΔUA in FIG. 2(a), 2(b)).

In the $^{13}$C-NMR spectrum (TMS as external reference), C1 of GlcUA and GalNAc were at about 97-104 ppm, while C1 peak of ΔUA was at about 103.5 ppm, chemical shift of C4 was 106.8 ppm, chemical shift of C5 was about 148.5 ppm.

It can be seen by the combination of the $^1$H NMR spectrum, $^{13}$C NMR spectrum and correlation spectra that in the main monosaccharide components of dLFG-1A, GlcUA and GalNAc were alternately linked via β(1→3) and β(1→4)glycosidic bonds to form its main chain, and thus make up a disaccharide structural unit of the main chain. It can be deduced according to the chemical shift of H2, H3 of GlcUA in combination with $^1$H-$^1$H ROESY, $^1$H-$^{13}$C HMBC that, Fuc was linked to GlcUAvia β(1→3) glycosidic bonds. Obviously, non-reducing end hexuronic acid was mainly ΔUA in dLFG-1A.

TABLE 2

Signal assignments of $^1$H $^{13}$C signals of dLFG-1A(δ [ppm])

| Position assignment | | $^1$H NMR (dLFG-1A) | $^{13}$C NMR | Position assignment | | $^1$H NMR (dLFG-1A) | $^{13}$C NMR |
|---|---|---|---|---|---|---|---|
| GalNAc-4S6S | 1 | 4.64 | 100.3 | GlcUA | 1 | 4.48 | 104.3 |
| | 2 | 4.04 | 51.7 | | 2 | 3.56 | 73.0 |
| | 3 | 3.93 | 76.1 | | 3 | 3.70 | 79.8 |
| | 4 | 4.83 | 77.4 | | 4 | 3.90 | 79.0 |
| | 5 | 3.98 | 72.6 | | 5 | 3.63 | 79.6 |
| | 6 | 4.22/ 4.13 | 67.6 | | 6 | / | 175.4 |
| | 7 | / | 175.4 | | | | |
| | 8 | 2.01 | 23.0 | | | | |
| ΔUA | 1 | 4.91 | 103.6 | Fuc-2S4S | 1 | 5.66/ 5.48 | 99.2/ 98.8 |
| | 2 | 3.88 | 72.3 | | 2 | 4.48/ 4.42 | 74.5 |
| | 3 | 4.48 | 71.1 | | 3 | 4.09 | 66.7 |
| | 4 | 5.76/ 5.82 | 106.8/ 107.1 | | 4 | 4.83 | 81.8 |
| | 5 | / | 148.0 | | 5 | 4.90 | 67.0 |
| | 6 | / | 175.4 | | 6 | 1.37/ 1.32 | 16.3 |
| Fuc-3S | 1 | 5.39 | 99.2 | Fuc-4S | 1 | 5.29 | 99.1 |
| | 2 | 4.11 | 71.3 | | 2 | 3.79 | 69.0 |
| | 3 | 4.60 | 81.7 | | 3 | 3.97 | 69.1 |
| | 4 | 4.18 | 69.9 | | 4 | 4.78 | 81.6 |
| | 5 | 4.46 | 67.6 | | 5 | 4.79 | 66.9 |
| | 6 | 1.36 | 16.1 | | 6 | 1.32 | 15.5 |

Wherein: GalNAc4S6S is 4,6-disulfated GalNAc; Fuc2S4S, -3S, -4S are -2,4-disulfated, -3-sulfated and -4-sulfated Fuc, respectively.

Example 2

Preparation of Depolymerized Fucosylated Glycosaminoglycan Derivatives (dLFG) with Series Molecular Weight by β-Elimination Depolymerization of TAG 2.1 Materials:

TAG from *Thelenotaanananas*, prepared according to the same method as Example 1. The other reagents were the same as Example 1.

2.2 Methods (1) Preparation of Quaternary Ammonium Salt of TAG:

5.02 g of quaternary ammonium salt of TAG was obtained according to the method of Example 1.

(2) Preparation of TAG Benzyl Esters with Different Benzyl Esterification Degrees:

The quaternary ammonium salt of TAG obtained in step (1) was dissolved in 50 mL of DMF under stirring, added with 25 mL of benzyl chloride, and reacted at 35° C. under stirring. About 15 mL of samples was taken at various reaction time points, respectively. To each of the solution samples, 100 mL of saturated NaCl-anhydrous ethanol (1:9, v/v) was added, centrifuged at 3500 rpm for 20 min. The obtained precipitation was washed with 50 mL saturated NaCl-anhydrous ethanol (1:9, v/v) for three times, and then dissolved in 40 mL of deionized water, dialyzed through a dialysis bag with molecular weight cutoff 3500 kD for 24 h. Each dialysis cutoff solution was TAG benzyl ester solution with different benzyl esterification degrees. The samples were lyophilized, and their esterification degrees were determined by $^1$H-NMR spectra as 9%, 21%, 28%, 45% and 56%, respectively.

(3) Preparation of Tetrabutylammonium Salt of TAG Benzyl Esters:

Each of the TAG benzyl ester solution with different benzyl esterification degrees obtained in step (2) was concentrated to 6 mL, converted into hydrogen type by exchange resin under the monitoring of conductivity meter, titrated with 0.4 M tetrabutylammonium hydroxide solution, so as to completely convert the sulfate groups and remnant carboxyl groups of esterification into tetrabutylammonium salt (a pH of about 7.5-8.0). Each of the resultant solution was lyophilized to obtain tetrabutylammonium salt of TAG benzyl esters with different esterification degrees, 1.523 g, 1.518 g, 1.493 g, 1.490 g and 1.731 g, respectively.

(4) Preparation of β-Elimination Depolymerization Products dLFG with Series Molecular Weights:

The tetrabutylammonium salt of TAG benzyl esters with different esterification degrees obtained in step (3) was added with DMF or $CH_2Cl_2$ and freshly prepared 100 mM NaOH-EtOH, according to the ratio of 50 mg of ammonium salts to 1 mL of DMF/$CH_2Cl_2$ and 1 mL of 0.1M NaOH/EtOH. The obtained solution was yellow and transparent, and reacted at 25° C. for 1 h under stirring. Then 1M HCl was quickly added to adjust to neutral pH to terminate the reaction. 2 mL of saturated sodium chloride and 20 mL of anhydrous ethanol were added to the solution, centrifuged at 3500 rpm for 15 min. The supernatant was removed and the precipitation was collected. The obtained precipitation was dissolved in 4 mL of $H_2O$, treated with ion exchange resin to convert the product into hydrogen type, and then adjusted with 0.1M NaOH to pH 7-8.

(5) Purification of β-Elimination Depolymerization Products with Series Molecular Weights:

Each of the solution obtained in step (4) was transferred into a 1 KD dialysis bag to perform dialysis with deionized water for 24 h followed by lyophilization to obtain β-elimination depolymerization products with series molecular weights, dLFG-1B, dLFG-1C, dLFG-1D, dLFG-1E and dLFG-1F.

(6) Determination of dLFG-1 Product:

The molecular weight, —$OSO_3^-$/—$COO^-$ molar ratio and optical rotation of dLFG-1B, -1C, -1D, -1E and -1F were determined according to the same method as Example 1.

2.3 Results

The determination results of physicochemical properties of dLFG-1B, dLFG-1C, dLFG-1D, dLFG-1E and dLFG-1F are shown in Table 2. The determination results showed that, dLFG series products obtained from TAG from *Thelenotaananas* by β-elimination depolymerization had relatively high yield and narrow molecular weight distribution. The determination results of conductivity method showed that there was no significant change in sulfate groups, and intrinsic viscosity was decreased with the decrease of molecular weight.

TABLE 2

Determination of monosaccharide compositions and physicochemical properties of dLFG with series molecular weights

| Sample | Molecular weight and distribution coefficient | | | —$OSO_3^-$/$COO^-$ | Optical rotation ($[\alpha]_D^{20}$, c = 1%) |
|---|---|---|---|---|---|
| | $M_w$ (Da) | $M_n$ (Da) | PDI | | |
| dLFG-1B | 22,096 | 14,919 | 1.481 | 3.56 | −56.8° |
| dLFG-1C | 13,966 | 9,766 | 1.432 | 3.42 | −54.5° |
| dLFG-1D | 11,255 | 8,233 | 1.367 | 3.51 | −51.5° |
| dLFG-1E | 7,066 | 4,973 | 1.421 | 3.48 | −49.8° |
| dLFG-1F | 5,339 | 3,844 | 1.389 | 3.62 | −43.9° |

Example 3

Preparation of β-Elimination Depolymerization Products of FGAG from Different Sea Cucumbers 3.1 Materials Each dry body wall of *Apostichopusjaponicus, Holothuriaedulis, Ludwigothureagrisea, Holothurialeucospilota* and *Holothurianobilis* was commercially available.

3.2 Methods (1) The each dry body wall of *Apostichopusjaponicus, Holothuriaedulis, Ludwigothureagrisea, Holothurialeucospilota* and *Holothurianobilis* was crushed. 300 g of each crushed materials was taken and extracted to obtain FGAG therefrom according to the method of Example 1(1), and designated as AJG, HEG, LGG, HLG and HNG, respectively.

(2) About 1 g of each of AJG, HEG, LGG, HLG and HNG was used to prepare β-elimination depolymerization products dLFG according to the method of Example 1 (2)-(5), and designated as dAJG, dHEG, dLGG, HLG and dHNG, respectively. The basic steps of β-elimination depolymerization of FGAG are shown in FIG. 12.

3.3 Results

Figure 7:
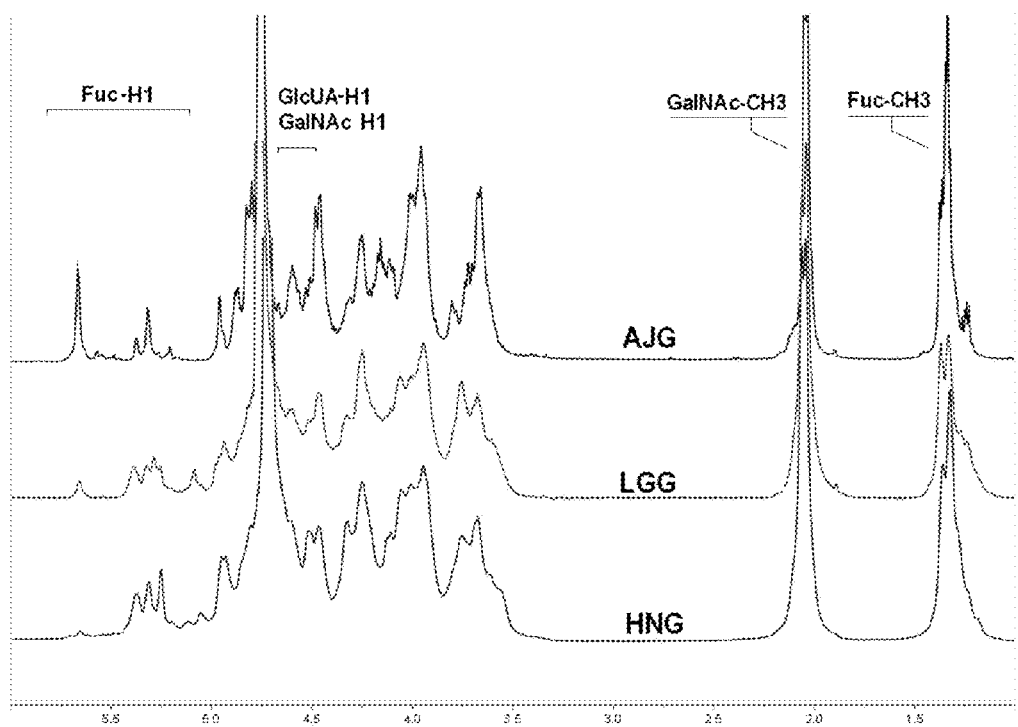
FIG. 7 shows $^1$H NMR spectra of AJG, LGG and HNG.

The yields of AJG, HEG, LGG, HLG and HNG isolated and purified from the dry body wall of *Apostichopusjaponicus, Holothuriaedulis, Ludwigothureagrisea, Holothurialeucospilota*, and *Holothurianobilis* were about 1.4%, 0.9%, 0.8% and 1.1%, respectively, and the weight-average molecular weights were all between about 50 kD and 80 kD. The $^1$H NMR spectra of FIG. 7 of the present invention showed the basic features of AJG, LGG and HNG being FGAG compounds: the terminal groups and the related characteristic proton signals of α-L-Fuc, β-D-GalNAc and β-D-GlcUA were clear and unambiguous.

Figure 8:
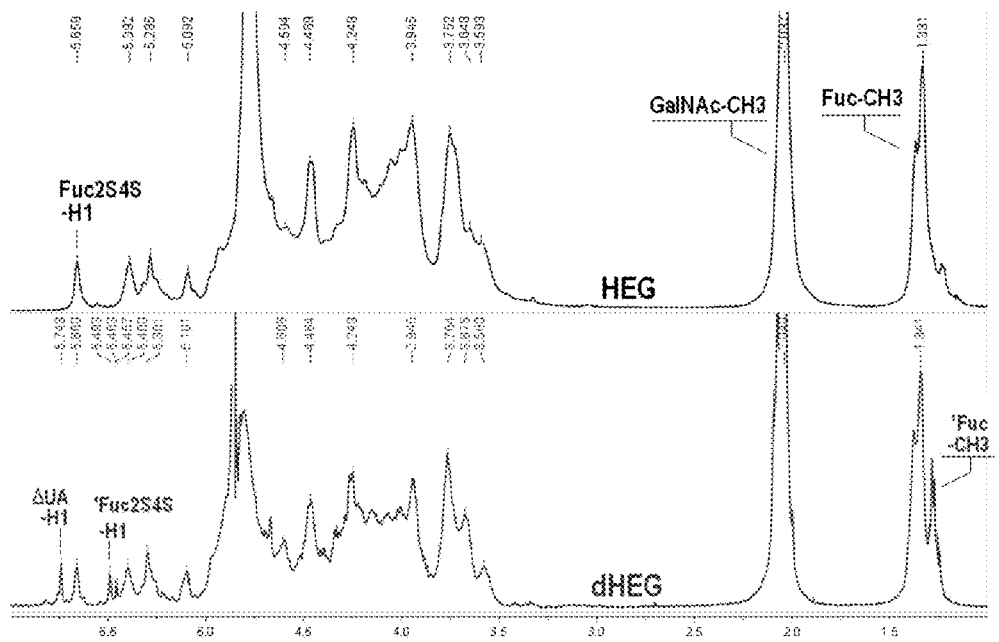
FIG. 8 shows $^1$H NMR spectra of HEG and dHEG.

The yields of dAJG (8.6 kD), dHEG (11.5 kD), dLGG (9.3 kD), HLG (10.2 kD) and dHNG (9.7 kD) prepared from AJG, HEG, LGG, HLG and HNG in step (2) were about 70%-90%. The $^1$H NMR of HEG and dHEG of FIG. 8 of the present invention showed the related characteristic signals of non-reducing terminal ΔUA formed by β-elimination depolymerization.

Example 4

Preparation of Terminal Reduced Product of dAJG 4.1 Materials dAJG, 8.6 kD, prepared according to the same method as Example 3. Sodium borohydride was commercially available analytical pure reagent.

4.2 Methods 500 mg of dAJG and 250 mg of NaBH$_4$ were dissolved in 20 mL of 0.1M NaOH solution, respectively. The NaBH$_4$ solution was added in the dAJG solution, and the obtained solution was stirred overnight at room temperature, then 200 mg of NaBH$_4$ was added and stirred for another 5 h. Then, 1M HCl was added to adjust pH from about 10.3 to about 2.5 (to destroy the excess sodium borohydride), and 1M NaOH was used to adjust pH back to neutral. Then 150 mL of anhydrous ethanol was added, centrifuged and the supernatant was removed. The precipitant was washed with 50 mL of anhydrous ethanol for twice, and then dissolved in 20 mL of deionized water, dialyzed in deionized water through a 3 kD dialysis bag overnight, and the cutoff solution of dialysis was lyophilized to obtain the terminal reduction product, rdAJG.

4.3 Results

The obtained rdAJG was about 386.3 mg. The determination results of DNS (3,5-dinitrosalicylic acid) method showed that all the terminals of rdAJG were substantially reduced.

Example 5

Preparation of dLFG-2A, the Terminal Reductive Amination Product of dLFG-1A 5.1 Materials dLFG-1A: prepared according to Example 1. Tyramine, sodium cyanoborohydride and other reagents were commercially available analytical pure reagents.

5.2 Methods (1) Terminal Reductive Amination of dLFG-1A:

0.1 g of dLFG-1A obtained in Example 1 was dissolved in 3.5 mL of 0.2 mM phosphate buffer (pH8.0), added with excess 80 mg of tyramine and 30 mg of sodium cyanoborohydride under stirring, reacted at 35° C. in water bath for about 72 h. After completion of the reaction, 10 mL of 95% ethanol was added, centrifuged to obtain precipitation. The obtained precipitation was washed with 30 mL of 95% ethanol for twice, re-dissolved in 35 mL of 0.1% NaCl, centrifuged to remove the insoluble matters. The supernatant was placed in a 1 kD dialysis bag and dialyzed with deionized water for 24 h, and lyophilized. 82 mg dLFG-2A was obtained.

(2) Physicochemical properties and spectra determination: The molecular weight and distribution were determined by HPGPC. The molar ratio of —OSO$_3^-$/—COO$^-$ was determined by conductometric method. The content of acetyl galactosamine (D-GalNAc) was determined by Elson-Morgon method. The content of glucuronic acid (D-GlcUA) was determined by carbazole method. The molar ratio of D-GalNAc/L-Fuc was calculated by $^1$HNMR methyl peak area (the same as Example 1). The NMR spectra were measured with a Bruker AVANCE AV 500 superconducting nuclear magnetic resonance instrument (500 MHz, Switzerland).

5.3 Results

Figure 9:
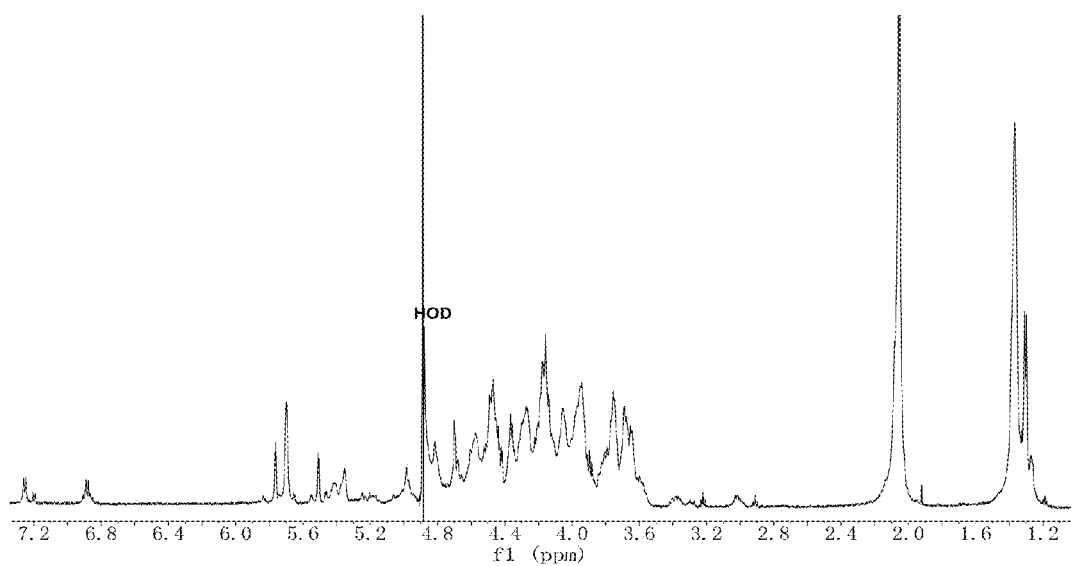
FIG. 9 shows $^1$H NMR spectra of dLFG-2A.

The yield of the product dLFG-2A was about 82%, based on the charging amount of dLFG-1A. The results of component determination of the product showed that, D-GalNAc:D-GlcUA:L-Fuc:—OSO$_3^-$ was about 1.00:0.98:1.10:3.60. Mw was about 8,969 Da, PDI was about 1.42, which agreed with the calculated results that LGC-1A structural unit had a polymerization degree of about 10. The $^1$HNMR spectrum of dLFG-2A is shown in FIG. 9. $^1$HNMR (D$_2$O, δ[ppm]): 7.25 (2', 6'H); 6.83 (3', 5'H); 5.65, 5.36, 5.28 (L-Fucα1H); 3.38 (8'H); 2.82 (7'H); 2.02 (D-GalNAc, CH$_3$); 1.30-1.32 (L-Fuc, CH$_3$). The integral of hydrogen of benzene ring to H4 of ΔUA was bout 1:0.28, which showed that the reducing terminals of the obtained product were completely reductively tyr-aminated.

Example 6

Preparation of Reductive Alkylation Product dHEG-PMP 6.1 Materials

HEG: FGAG compounds from *Holothuriaedulis*, prepared according to the method of step (1) of Example 3. 1-phenyl-3-methyl-5-pyrazolone (PMP) was biochemical reagent with 99% purity.

6.2 Methods and Results 100 mg of HEG was processed according to the same method as step (3) (4) of Example 1 to obtain 132 mg of HEG benzyl estertetrabutylammonium salt. The obtained HEG benzyl estertetrabutylammonium salt was dissolved in DMF (50 mg/mL), added with EtONa-EtOH (a final concentration of 20 mM) and reacted at 50° C. for 0.5 h under stirring; added with 10 mL of 0.5 mol/L PMP methanol solution and reacted for another 1.5 h under stirring; and then added with 10 mL of water and cooled to room temperature under stirring. The reaction solution was neutralized with 1M HCl, and added with 20 mL of saturated sodium chloride and 200 mL of anhydrous ethanol, centrifuged to remove supernatant. The obtained precipitation was dissolved in 10 mL of water, dialyzed through a 3 kD dialysis bag, and lyophilized, and 102 mg of dHEG-PMP product was obtained.

It was calculated according to the $^1$HNMR spectrum of dHEG-PMP that the terminals of the product were completely reductively alkylated.

Example 7

Anticoagulant Activity of dLFG from TAG 7.1 Materials

Samples: Series samples dLFG-1A-1F, dLFG-2A, and dLFG-1G with a Mw of about 3.5 kD prepared from TAG by β-elimination method of Examples 1, 2 and 5.

Reagents: Enoxaparin sodium injection (LMWH, Mw 3500-5500, Sanofi Aventis); coagulation control plasma, activated partial thromboplastin time (APTT) assay kit, thrombin time (TT) assay kit, prothrombin time assay kit (PT-dry powder), manufactured by German TECO GmbH company; other reagents, commercially available analytical pure.

Instrument: MC-4000 coagulometer (MDC, Germany).

5.2 Methods

The sample was dissolved in deionized water according to their actual situations to prepare series concentration of solution. The anticoagulant activities of series dLFG compounds were determined by MC-4000 coagulometer according to the instructions of APTT, PT and TT assay kits.

5.3 Results

The anticoagulant experiment results of dLFG-1A-1F and dLFG-2A are shown in Table 4.

The results in Table 4 showed that both dLFG-1A-1F and dLFG-2A can significantly prolong human plasma APTT, the required drug concentrations thereof for doubling the APTT (time was doubled) were all less than 9 μg/mL, which had stronger activities than Enoxaparin sodium (9.3 μg/mL), indicating that all these derivatives can inhibit intrinsic coagulation effectively.

The results also showed that dLFG-1A~1F and dLFG-2A had less influence on PT and TT, the influence were weaker than that of the positive drug Enoxaparin sodium, indicating that these derivatives had less influence on extrinsic coagulation pathway and common coagulation pathway.

It can be seen from the comparison of the molecular weight and the activity intensity of prolonging APTT of series dLFG compounds that the anticoagulant activity was enhanced with the increase of the molecular weight. Therefore, molecular weight was one of the most important factors that influence the anticoagulant activity of the series compounds. Generally, considering the anticoagulant activity, based on weight average molecular weight, the preferred molecular weight of the dLFG of the present invention should be not less than 3,000 Da.

TABLE 4

Anticoagulant activity of series dLFG with different molecular weights

| Compounds | Weight average molecular weight (Mw) | Drug concentration for doublingAPTT (μg/mL) | $PT^a$ (s) | $TT^b$ (s) |
|---|---|---|---|---|
| dLFG-1A | 8,798 | 4.26 | 14.2 | 16.3 |
| dLFG-1B | 22,096 | 3.26 | 14.3 | 19.1 |
| dLFG-1C | 13,966 | 3.46 | 14.1 | 16.9 |
| dLFG-1D | 11,255 | 3.78 | 14.7 | 18.2 |
| dLFG-1E | 7,066 | 3.90 | 14.3 | 16.6 |
| dLFG-1F | 5,339 | 4.86 | 14.3 | 16.2 |
| dLFG-1G | 3,521 | 8.15 | 14.5 | 16.3 |
| dLFG-2A | 8,969 | 3.57 | 14.1 | 16.5 |

$^a$PT value at a drug concentration of 25 μg/mL (PT value of blank control group was 14.4 ± 0.2 s);
$^b$TT value at a drug concentration of 12.5 μg/mL (TT value of blank control group was 16.0 ± 0.3 s).

Example 8

Effect of dLFG on the Activity of Coagulation Factors 8.1 Materials

Samples: dLFG-1A~dLFG-1F, the same as Example 7.

Reagents: human control plasma (TECO GmbH company, German); Enoxaparin sodium injection (LMWH, MW 3500-5500, Sanofi-Aventis); Heparin (Mw~18000, sigma); oversulfated chondroitin sulfate (OSCS, the National Institute for the Control of Pharmaceutical and Biological Products); thrombin (f.IIa) 100 NIHU/mg, chromogenic substrate for thrombin detection (CS-0138) 25 mg/vial, heparin cofactor II (HC-II) 100 μg/vial, all from HYPHEN BioMed (France); Factor VIII (f.VIII) 200 IU/vial, Shanghai RAAS blood products Co., Ltd.; f.VIII detection kit, including Reagents: R1: Human Factor X; R2: Activation Reagent, human Factor IXa, containing human thrombin, calcium and synthetic phospholipids; R3: SXa-11, Chomogenic substrate, specific for Factor Xa; R4: Tris-BSA Buffer; HYPHEN BioMed (France); Pefachrome® FXIIa-5963 (CENTERCHEM, INC).

Instrument: Bio Tek-ELx 808 microplate reader (U.S.).

8.2 Methods (1) Determination of Inhibition Activity of Intrinsic Tenase (f.Xase):

The detection method was established using f.VIII assay kit in combination with f.VIII reagent. 30 μL of series concentration of dLFG-1A~F solution or control solvent (Tris-BSA buffer $R_4$) was mixed with 2.0 IU/mL f.VIII (30 μL), added with $R_2$ (30 μL), $R_1$ (30 μL) sequentially, incubated at 37° C. for 2 min, and then added with $R_3$ (30 μL), incubated accurately at 37° C. for 2 min. $OD_{405\ nm}$ was measured. $EC_{50}$ of inhibition f.Xase inhibition of each sample was calculated by the method of reference (Sheehan J. P. & Walke E. K., *Blood,* 2006, 107:3876-3882).

(2) Determination of HC-II-Dependent Anti-Thrombin (f.IIa) Activity:

30 μL of series concentration of dLFG-1A~dLFG-1F solution or control solution (Tris-HCl buffer) was added into 96 well microtiter plates, added with 30 μL of 1 μM HC-II, mixed, incubated at 37° C. for 1 min; and then added with 30 μL of 10 U/mL IIa, incubated at 37° C. for 1 min; added with 30 μL of 4.5 mM chromophoric substrate CS-0138, mixed, incubated accurately at 37° C. for 2 min. $OD_{405\ nm}$ was measured. ΔOD was calculated according to blank control (Tris-HCl). $EC_{50}$ value of anti-thrombin of each sample was calculated according to the method of reference (Sheehan J. P.& Walke E. K., *Blood,* 2006, 107:3876-3882).

(3) Determination of Activation Activity of Factor XII:

The activity of f.XII was determined according to the method of reference (Hojima et al., *Blood,* 1984, 63:1453-1459) but with a little change. 30 μL of series concentration of dLFG-1A~dLFG-1F solution or control solution (20 mM Tris-HCl buffer, pH7.4) was added to 96 well microtiter plates, added with 30 μL of 312 nM human coagulation factor XII (containing 1 mM NaAc—HCl and 40 mM NaCl/0.02% $NaN_3$, pH 5.3), mixed, incubated at 37° C. for 1 min; and then added with 30 μL of 620 nM pre-kallikrein, incubated at 37° C. for 1 min; added with 30 μL of 6 mM kallikrein chromophoric substrate, mixed, incubated at 37° C. and $OD_{405\ nm}$ was measured at a specified time interval. Change rate of OD value was calculated.

8.3 Results

The effect of dLFG-1A~dLFG-1F on coagulation factors is shown in Table 5.

Figure 10:
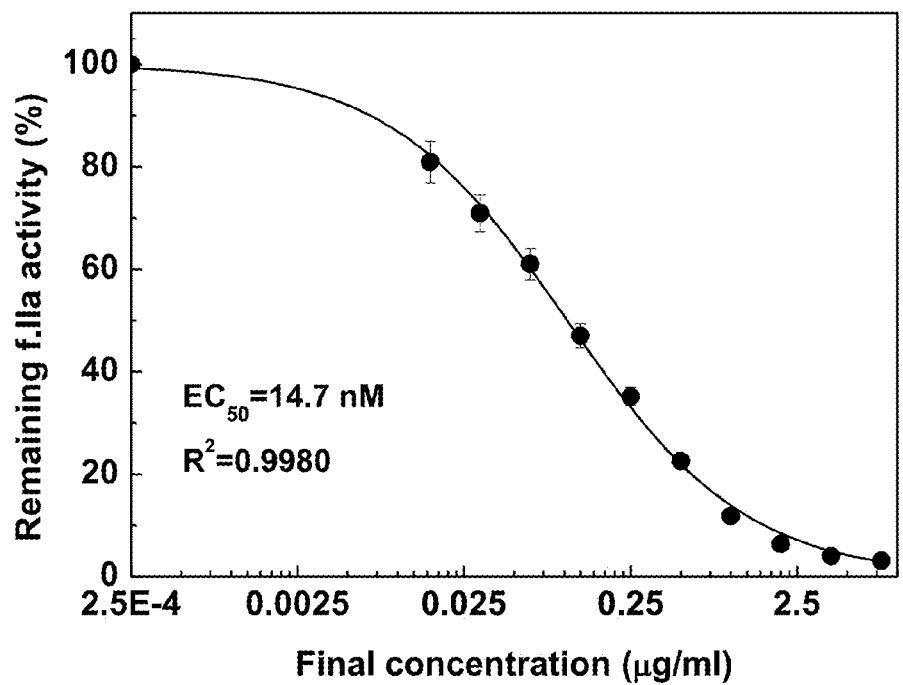
FIG. 10 shows dose-response relationship of HC-II dependent anti-thrombin activity of dLFG-1E.
Figure 11:
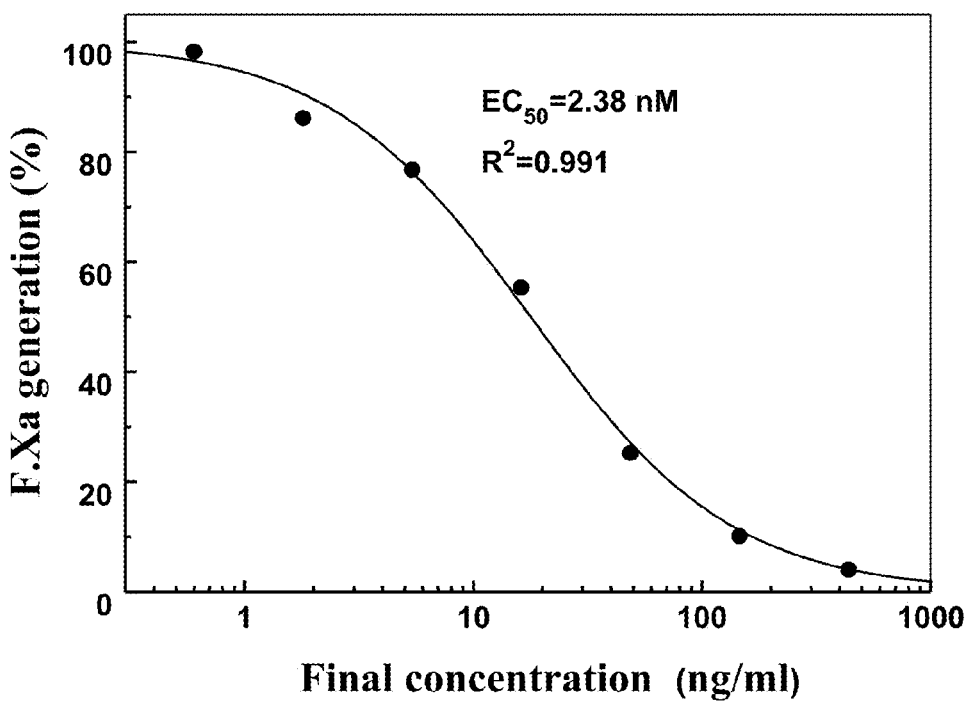
FIG. 11 shows dose-response relationship of f.Xase inhibition activity of dLFG-1E.

FIG. 10 and FIG. 11 showed dose-response relationship of dLFG-1E on HC-II dependent anti-thrombin activity and f.Xase inhibitory activity, respectively.

TABLE 5

Effect of series dLFG compounds on coagulation factors

| Compounds | Weight average molecular weight | Anti-f.Xase ($EC_{50}$) | | Anti IIa ($EC_{50}$) | |
|---|---|---|---|---|---|
| | | (ng/mL) | (nM) | (ng/mL) | (nM) |
| dLFG-1A | 8,798 | 13.5 | 1.53 | 159 | 18.1 |
| dLFG-1B | 22,096 | 11.6 | 0.52 | 122 | 5.5 |
| dLFG-1C | 13,966 | 11.8 | 0.84 | 140 | 10.0 |
| dLFG-1D | 11,255 | 11.5 | 1.02 | 134 | 11.9 |
| dLFG-1E | 7,066 | 16.8 | 2.38 | 104 | 14.7 |
| dLFG-1F | 5,339 | 25.5 | 4.78 | 210 | 39.3 |

Figure 5:
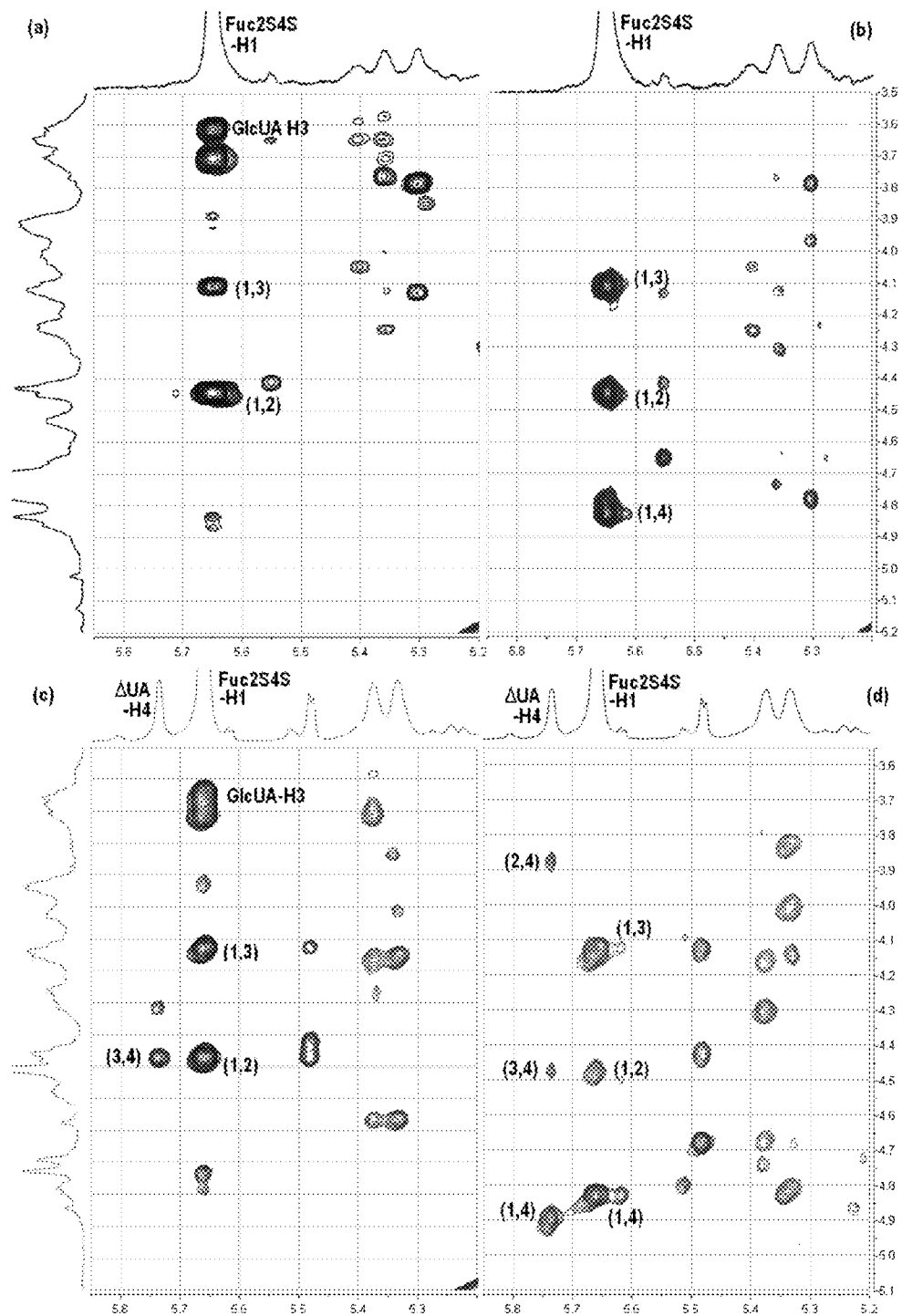
FIG. 5(a) shows $^1$H-$^1$H ROESY spectrum of TAG.
FIG. 5(b) shows $^1$H-$^1$H TOCSY spectrum of TAG.
FIG. 5(c) shows $^1$H-$^1$H ROESY spectrum of dLFG-1A.
FIG. 5(d) shows $^1$H-$^1$H TOCSY spectrum of dLFG-1A.
Figure 6:
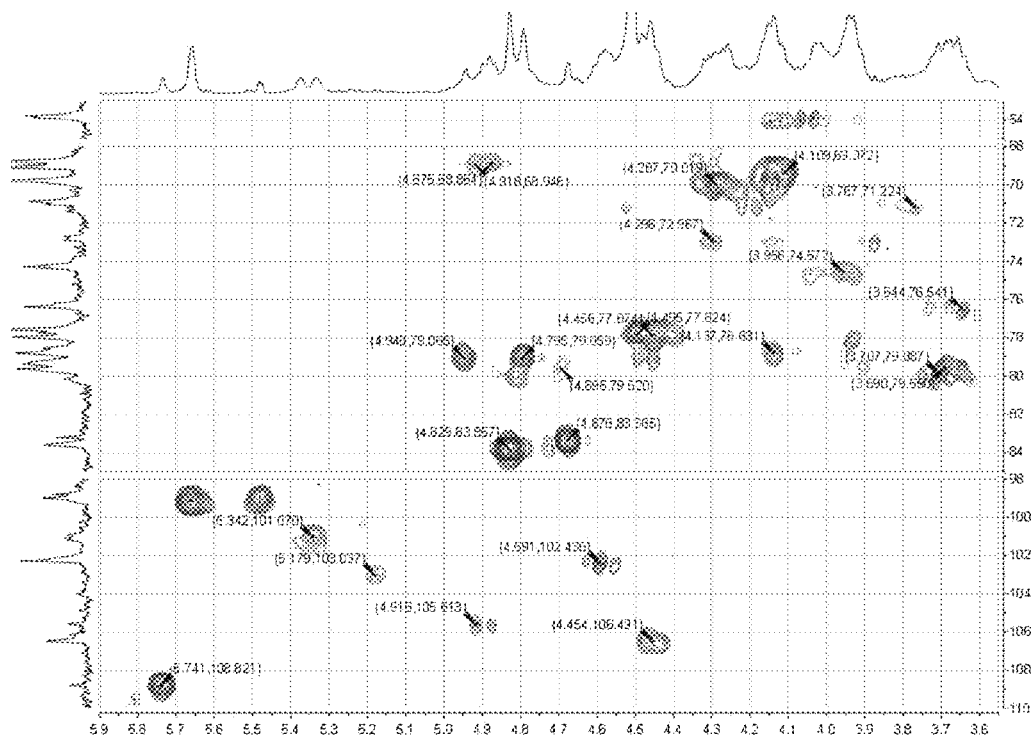
FIG. 6 shows $^1$H-$^{13}$C HSQC spectrum of dLFG-1A.

Table 5, FIGS. 4 and 5 showed that the dLFG-1A~dLFG-1F prepared by the invention had potent anti-f.Xase activity and the effective concentration for inhibiting 50% f.Xase activity ($EC_{50}$) was about 0.5-5 nM. Meanwhile, it also had a significant HC-II dependent anti-thrombin activity, its $EC_{50}$ was about 5.5-40 nM. Since factor Xase is the last target of intrinsic coagulation pathway in coagulation cascade and is the rate-limiting step of the coagulation process, it may be the key mechanism of the potent anticoagulant activity of these compounds.

Recent studies show that the selective intrinsic coagulation factor inhibitors can effectively avoid the bleeding tendency while producing antithrombotic activity; therefore, the dLFG compounds of the present invention have potential antithrombotic application value.

In addition, the f.XII activation can lead to serious adverse symptoms such as hypotension by activating pre-kallikrein, and clinical events caused by oversulfated chondroitin sulfate (OSCS) pollution were given concern. The research results of the present invention showed that, unlike OSCS, the dLFG-1A~dLFG-1F of the present invention do not have significant activity of f.XII activation at an effective anticoagulant dosage.

Example 9

Aqueous Solution for Injection of Low-Molecular-Weight Fucosylated Glycosaminoglycan 9.1 Materials
dLFG-1E was prepared according to the method of Example 2. Mw: 7,066 Da.
9.2 Formula

| raw material and excipient | Dosage |
| --- | --- |
| dLFG-1E | 50 g |
| Water for injection | 1000 mL |
| Prepared into | 1000 vials |

9.3 Preparation Process
The formulated low-molecular-weight fucosylated glycosaminoglycan sodium salt was weighed, added with water for injection to full capacity, stirred to dissolve completely, and subjected to interval autoclaving sterilization. 0.6% pharmaceutical activated carbon was added and stirred for 20 min. A Buchner funnel and a 3.0 μm micro porous filter membrane were used for decarbonization filtration to remove pyrogens. The content of the intermediate was tested. The qualified products were passed through a 0.22 μm micro-porous filter membrane, filled into penicillin bottles with 1 mL for each bottle, while monitoring the filling volume during filling; inspected qualification, and packed to obtain the final products.

Example 10

Freeze-Dried Powder for Injection of Low-Molecular-Weight Fucosylated Glycosaminoglycan 10.1 Materials
dLFG-2A was prepared according to the method of Example 2. Mw: 8,969 Da.
10.2 Formula

| raw material and excipient | Dosage |
| --- | --- |
| dLFG-2A | 50 g |
| Water for injection | 500 mL |
| Prepared into | 1000 vials |

10.3 Preparation Process
The formulated low-molecular-weight fucosylated glycosaminoglycan sodium salt was weighed, added with water for injection to full capacity, stirred to dissolve completely, and subjected to interval autoclaving sterilization. 0.6% pharmaceutical activated carbon was added and stirred for 20 min. A Buchner funnel and a 3.0 μm micro porous filter membrane were used for decarbonization filtration to remove pyrogens. The content of the intermediate was tested. The qualified products were passed through a 0.22 μm micro-porous filter membrane, filled into penicillin bottles with 0.5 mL for each bottle, partially stoppered, and transported into a lyophilizer and lyophilized according to the predetermined freeze-drying curve, complete stoppered, withdrawn from the lyophilizer, capped, inspected to be qualified, to obtain the final products.

Lyophilization procedure: The samples were placed into the lyophilizer; the temperature of shelves was dropped to −40° C., maintaining for 3 h; the temperature of cold trap was dropped to −50° C.; then the vacuum was pumped to 300 μbar.

Sublimation: the temperature was increased uniformly to −30° C. within 1 h, maintaining for 2 h; increased uniformly to −20° C. within 2 h, maintaining for 8 h; the vacuum was maintained at 200-300 μbar. Drying: the temperature was increased to −5° C. within 2 h, maintaining for 2 h, and the vacuum was maintained at 150-200 μbar; the temperature was increased to 10° C. within 0.5 h, maintaining for 2 h, and the vacuum was maintained at 80-100 μbar; the temperature was increased to 40° C. within 0.5 h, maintaining for 4 h, and the vacuum was reduced to the lowest.

What is claimed is:

1. A low-molecular-weight glycosaminoglycan derivative or a pharmaceutically acceptable salt thereof, wherein:

monosaccharide components of the low-molecular-weight glycosaminoglycan derivative comprise hexuronic acid, hexosamine, deoxyhexamethylose and the sulfate forms of those monosaccharides; wherein, the hexuronic acid is D-glucuronic acid and $\Delta^{4,5}$-hexuronic acid (4-deoxy-threo-hex-4-enepyranosyluronic acid), the hexosamine is acetylgalactosamine (2-N-acetylamino-2-deoxy-D-galactose) or a terminal reduction product thereof, the deoxyhexamethylose is L-fucose;

based on molar ratio, the ratio of each monosaccharide and —$OSO_3^-$ in the low-molecular-weight glycosaminoglycan derivative is hexuronic acid: hexosamine: deoxyhexamethylose: sulfate group=1: (1±0.3): (1±0.3): (3.0±1.0); in the hexuronic acid, based on molar ratio, the percentage of $\Delta^{4,5}$-hexuronic acid is not less than 2.5% of the total hexuronic acid;

the low-molecular-weight glycosaminoglycan derivative has a weight average molecular weight (Mw) of 3 kD-20 kD;

the low-molecular-weight glycosaminoglycan derivative has a polydispersity index of between 1.0 and 1.8; and the low-molecular-weight glycosaminoglycan derivative is a mixture of the homologous glycosaminoglycan derivatives having a structure of Formula (I),

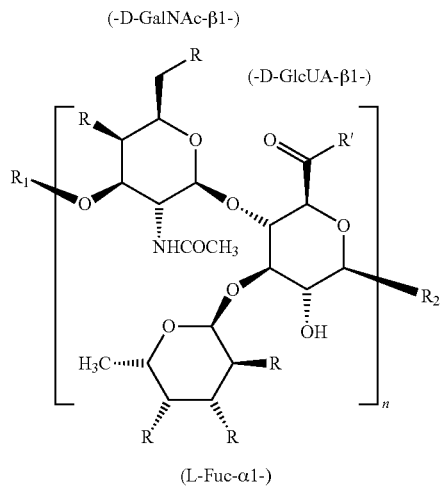

(I)

in Formula (I):

n is an integer with average value of 2-20;

-D-GlcUA-β1- is -D-glucuronic acid-β1-yl;

-D-GalNAc-β1- is -2-deoxy-2-N-acetylamino-D-galactose-β1-yl;

L-Fuc-α1- is -L-fucose-α1-yl;

ΔUA-1- is $\Delta^{4,5}$-hexuronic acid-1-yl (4-deoxy-threo-hex-4-enepyranosyluronic acid-1-yl);

R is —OH or —$OSO_3^-$;

R' is —OH, C1-C6 alkoxy, or C7-C10 aryloxy;

$R_1$ is a group shown in Formula (II) or (III), and in said mixture, based on molar ratio, the ratio of the compounds that $R_1$ is Formula (II) to the compounds that $R_1$ is Formula (III) is not less than 2:1;

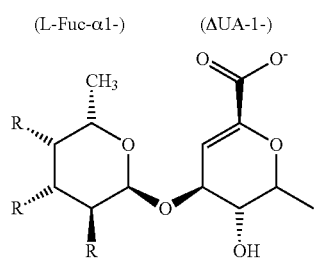

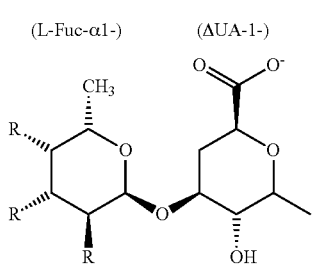

wherein, R and R' are defined as above;

$R_2$ is a group shown in Formula (IV) or (V),

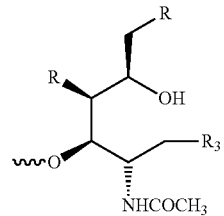

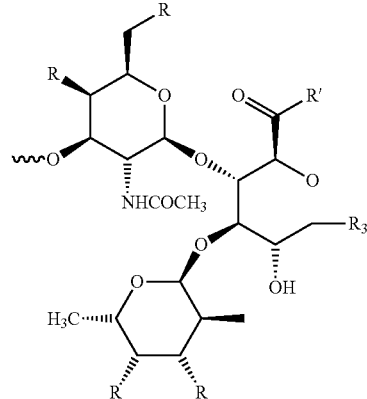

wherein, R and R' are defined as above;

$R_3$ is carbonyl, hydroxyl, C1-C6 alkoxy, C1-C6 alkoxycarbonyl, C6-C12 aryl, substituted or non-substituted five or six membered nitrogen-containing heterocyclic group, or —$NHR_4$; wherein $R_4$ in —$NHR_4$ is substituted or non-substituted straight or branched chain C1-C6 alkyl, substituted or non-substituted C7-C12 aryl, substituted or non-substituted heteroatom-containing heterocyclic aryl.

2. The low-molecular-weight glycosaminoglycan derivative or a pharmaceutically acceptable salt thereof according to claim 1, wherein the low-molecular-weight glycosaminoglycan derivative has a weight average molecular weight of 5 kD-12 kD; the low-molecular-weight glycosaminoglycan derivative has a polydispersity index of between 1.1 and 1.5.

3. The low-molecular-weight glycosaminoglycan derivative or a pharmaceutically acceptable salt thereof according to claim 1, wherein the low-molecular-weight glycosaminoglycan derivative is a β-elimination depolymerization product of fucosylated glycosaminoglycan from body wall and/or viscera of an echinoderm of the class Holothuroidea, or a derivative obtained by reduction of the reducing terminal of the depolymerized product.

4. The low-molecular-weight glycosaminoglycan derivative or a pharmaceutically acceptable salt thereof according to claim 3, wherein the echinoderm of the class Holothuroidea includes:

*Apostichopusjaponicus;*
*Actinopygamauritiana;*
*Actinopygamiliaris;*
*Acaudinamolpadioides;*
*Bohadschiaargus;*
*Holothuriaedulis;*
*Holothurianobilis;*
*Holothurialeucospilota;*
*Holothuriasinica;*
*Holothuriavagabunda;*

*Isostichopusbadionotus;*
*Ludwigothureagrisea;*
*Stichopuschloronotus;*
*Thelenotaananas;*
*Thelenotaanax.*

5. The low-molecular-weight glycosaminoglycan derivative or a pharmaceutically acceptable salt thereof according to claim 1, wherein the pharmaceutically acceptable salt is an alkali metal salt, an alkaline-earth metal salt and an organic ammonium salt of the low-molecular-weight glycosaminoglycan derivative.

6. The low-molecular-weight glycosaminoglycan derivative or a pharmaceutically acceptable salt thereof according to claim 5, wherein the pharmaceutically acceptable salt is sodium salt, potassium salt or calcium salt of the low-molecular-weight glycosaminoglycan derivative.

7. A pharmaceutical composition comprising an anticoagulant effective amount of the low-molecular-weight glycosaminoglycan or a pharmaceutically acceptable salt thereof according to claim 1, and a pharmaceutical excipient.

8. The pharmaceutical composition according to claim 7, wherein a dosage form of said pharmaceutical composition is water solution for injection or lyophilized powder for injection.

* * * * *